US009107588B2

(12) United States Patent
Katayama et al.

(10) Patent No.: US 9,107,588 B2
(45) Date of Patent: *Aug. 18, 2015

(54) CONTINUOUS POSITIONING APPARATUS AND METHODS

(71) Applicant: Tensys Medical, Inc., San Diego, CA (US)

(72) Inventors: Andrew S. Katayama, Cardiff-by-the-sea, CA (US); Todd A. Keitel, Carlsbad, CA (US); Manouchehr Goharlaee, Encinitas, CA (US); Stuart L. Gallant, San Diego, CA (US); Warren B. Craycroft, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/965,058

(22) Filed: Aug. 12, 2013

(65) Prior Publication Data

US 2014/0046201 A1    Feb. 13, 2014

Related U.S. Application Data

(63) Continuation of application No. 11/803,559, filed on May 14, 2007, now Pat. No. 8,506,497.

(60) Provisional application No. 60/800,164, filed on May 13, 2006.

(51) Int. Cl.
*A61B 5/021* (2006.01)
*A61B 5/0225* (2006.01)
*A61B 5/00* (2006.01)

(52) U.S. Cl.
CPC ............. *A61B 5/0225* (2013.01); *A61B 5/021* (2013.01); *A61B 5/6843* (2013.01)

(58) Field of Classification Search
CPC .... A61B 5/7264; A61B 5/0225; A61B 5/021; A61B 5/6843
USPC .................................................. 600/485–507
See application file for complete search history.

(56) References Cited

U.S. PATENT DOCUMENTS 4,869,261 A    9/1989 Penaz
5,261,414 A    11/1993 Aung et al.
(Continued)

FOREIGN PATENT DOCUMENTS

EP    0818176    1/1998
JP    8080285     3/1996
(Continued)

OTHER PUBLICATIONS

R.A. Rutenbar, "Simulated annealing algorithms: an overview," IEEE Circuits Devices Mag., No. 1, pp. 19-26, Jan. 1989.
(Continued)

*Primary Examiner* — Navin Natnithithadha
*Assistant Examiner* — Eric Messersmith
(74) *Attorney, Agent, or Firm* — Gazdzinski & Associates PC

(57) ABSTRACT

Improved apparatus and methods for non-invasively assessing one or more parameters associated with systems such as fluidic circulating systems (e.g., the circulatory system of a living organism). In a first aspect, an improved method of continuously measuring pressure from a compressible vessel is disclosed, wherein a substantially optimal level of compression for the vessel is achieved and maintained using dynamically applied dither perturbations (e.g., modulation) on the various axes associated with the vessel. In a second aspect, an improved apparatus and method are provided for monitoring hemodynamic parameters, such as blood pressure, in a continuous and non-invasive manner while operating under a single unifying scheme. One variant of this scheme using a simulated annealing (SA) type approach to determining and maintaining an optimal operating state.

19 Claims, 26 Drawing Sheets

(56) References Cited

U.S. PATENT DOCUMENTS

| | | | |
|---|---|---|---|
| 5,797,850 | A | 8/1998 | Archibald et al. |
| 5,848,970 | A | 12/1998 | Voss et al. |
| 5,964,711 | A | 10/1999 | Voss et al. |
| 6,176,831 | B1 | 1/2001 | Voss et al. |
| 6,228,034 | B1 | 5/2001 | Voss et al. |
| 6,290,650 | B1 | 9/2001 | Butterfield et al. |
| 6,322,516 | B1 | 11/2001 | Masuda et al. |
| 6,554,774 | B1 | 4/2003 | Miele |
| 6,673,062 | B2 | 1/2004 | Yee et al. |
| 6,676,600 | B1 | 1/2004 | Conero et al. |
| 6,730,038 | B2 | 5/2004 | Gallant et al. |
| 6,741,340 | B2 * | 5/2004 | Murakawa et al. ........... 356/138 |
| 6,974,419 | B1 | 12/2005 | Voss et al. |
| 7,048,691 | B2 | 5/2006 | Miele |
| 7,163,877 | B2 | 1/2007 | Niimi |
| 7,291,112 | B2 | 11/2007 | Martin |
| 7,317,409 | B2 | 1/2008 | Conero |
| 2002/0055680 | A1 | 5/2002 | Miele |
| 2004/0059234 | A1 * | 3/2004 | Martin et al. ................. 600/500 |
| 2004/0073123 | A1 | 4/2004 | Hessel |
| 2004/0152957 | A1 | 8/2004 | Stivoric et al. |
| 2005/0049820 | A1 | 3/2005 | Kirsch et al. |

FOREIGN PATENT DOCUMENTS

| | | |
|---|---|---|
| WO | 0003635 | 1/2000 |
| WO | 2007133759 | 11/2007 |

OTHER PUBLICATIONS

"A Monte Carlo Simulated Annealing Approach to Optimization Over Continuous Variables", Journal of Computational Physics, London, GB, vol. 56 No. 1, Nov. 1, 1984, pp. 259-271, XP024750505, ISSN: 0021-9991.

* cited by examiner

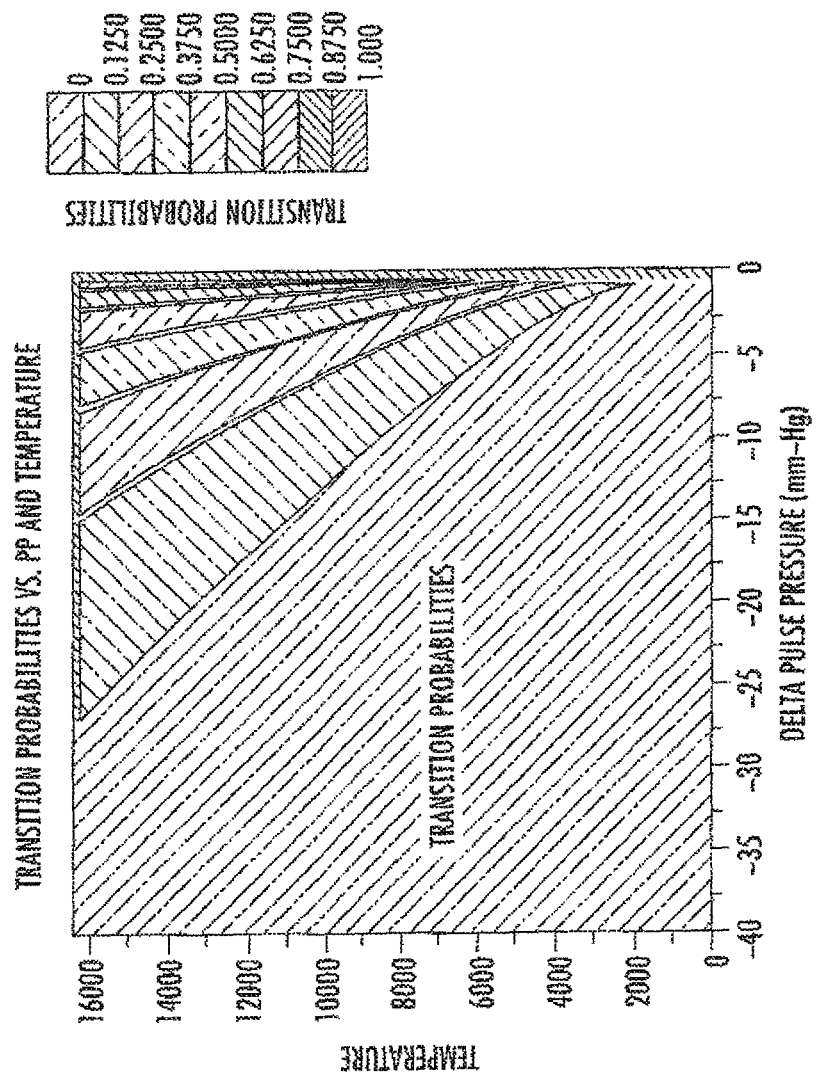

Average Mean to Temperature Tax chart

CONTINUOUS POSITIONING APPARATUS AND METHODS

PRIORITY

This application is a continuation of and claims priority to U.S. patent application Ser. No. 11/803,559 of the same title filed May 14, 2007, issuing as U.S. Pat. No. 8,506,497 on Aug. 13, 2013, which claims priority to U.S. Provisional Patent Application Ser. No. 60/800,164 filed May 13, 2006 of the same title, each of the foregoing being incorporated herein by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

1. Field of the Invention

This invention relates generally to methods and apparatus for monitoring parameters associated with fluid systems, and specifically in one aspect to the non-invasive monitoring of arterial blood pressure in a living subject.

2. Description of Related Technology

The accurate, continuous, non-invasive measurement of blood pressure has long been sought by medical science. The availability of such measurement techniques would allow the caregiver to continuously monitor a subject's blood pressure accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's peripheral (predominately brachial) artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from over-compression to under-compression or vice versa. At the onset of a decreasing applanation sweep, the artery is over-compressed into a "dog bone" shape, so that pressure pulses are not recorded. At the end of the sweep, the artery is under-compressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. Note that other measures analogous to maximum pulsatile pressure, including maximum rate of change in pressure (i.e., maximum dP/dT) can also be implemented.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This can result in inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement.

Tonometry systems are also commonly quite sensitive to the orientation of the pressure transducer on the subject being monitored. Specifically, such systems show degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Furthermore, compliance in various apparatus components (e.g., the strap and actuator assembly) and the lack of soft padding surrounding the sensor which minimizes edge effects may adversely impact the accuracy of tonometric systems to a significant extent.

One very significant limitation of prior art tonometry approaches relates to the magnitude and location of the applied applanation pressure during varying conditions of patient motion, position, mean pressure changes, respiration, etc. Specifically, even when the optimum level of arterial compression at the optimal coupling location is initially achieved, there is commonly real-world or clinical factors beyond reasonable control that can introduce significant error into the measurement process, especially over extended periods of time. For example, the subject being monitored may voluntarily or involuntarily move, thereby altering (for at least a period of time) the physical relationship between the tonometric sensor and the subject's tissue/blood vessel. Similarly, bumping or jarring of the subject or the tonometric measurement apparatus can easily occur, thereby again altering the physical relationship between the sensor and subject. The simple effect of gravity can, under certain circumstances, cause the relative positions of the sensor and subject blood vessel to alter with time as well.

Furthermore, physiologic responses of the subject (including, for example, relaxation of the walls of the blood vessel due to anesthesia or pharmacological agents) can produce the need for changes in the applanation level (and sometimes even the lateral/proximal position of the sensor) in order to maintain optimal sensor coupling. Additionally, due to the compliance of surrounding tissue and possibly measurement system, the applanation level often needs to adjust with changes in mean arterial pressure.

Several approaches have heretofore been disclosed in attempts to address the foregoing limitations. In one prior art approach, an occlusive cuff is used to provide a basis for periodic calibration; if the measured pressure changes a "significant" amount or a determined time has elapsed, then the system performs a cuff calibration to assist in resetting the applanation position. Reliable pressure data is not displayed or otherwise available during these calibration periods. See for example U.S. Pat. No. 5,261,414 to Aung, et al issued Nov. 16, 1993 and entitled "Blood-Pressure Monitor Apparatus," assigned to Colin Corporation (hereinafter "Aung"). See also U.S. Pat. No. 6,322,516 issued Nov. 27, 2001 and entitled "Blood-Pressure Monitor Apparatus," also assigned to Colin Corporation, wherein an occlusive cuff is used as the basis for calibration of a plurality of light sensors.

In another prior art approach, a pressure cuff or a pelotte equipped with a plethysmographic gauge, such as an impedance or a photo-electric device, is used to drive a servo control loop. See, e.g., U.S. Pat. No. 4,869,261 to Penaz issued Sep. 26, 1989 and entitled "Automatic noninvasive blood pressure monitor," assigned to University J. E. Purkyne v Brne (hereinafter "Penaz"). In this device, the sensor is connected through at least one amplifier and a phase corrector to an electro-pressure transducer. All these components constitute the closed loop of a servo control system which (at least ostensibly) continuously changes the pressure in the cuff and attempts to maintain the volume of the artery at a value corresponding to zero tension across the arterial wall. The servo control system loop further includes a pressure vibration generator, the frequency of vibration being higher than that of the highest harmonic component of blood pressure wave. A correction circuit is also provided, the input of which is connected to the plethysmographic sensor and output of which is provided to correct the setpoint of the servo control system. The Penaz system therefore in effect constantly "servos" (within a cardiac cycle) to a fixed light signal level received from the sensor. Unlike the Colin systems described above, the system continuously displays pressure to the operator. However, the operation of the plethysmographic sensor of Penaz limited the application of this device to a peripheral section of a limb (preferably a finger) where the peripheral pressure, especially under conditions of compromised peripheral circulation, may not accurately reflect aortic or brachial artery pressure. This presents a potentially significant cause of error.

Yet another prior art approach uses a series of varying pressure "sweeps" performed successively to attempt to identify the actual intra-arterial blood pressure. The applanation pressure applied during each of these sweeps is generally varied from a level of arterial under-compression to over-compression (or vice-versa), and the system analyzes the data obtained during each sweep to identify, e.g., the largest pressure waveform amplitude. See, e.g., U.S. Pat. No. 5,797,850 to Archibald, et al issued Aug. 25, 1998 and entitled "Method and apparatus for calculating blood pressure of an artery," assigned to Medwave, Inc. (hereinafter "Archibald"). The system of Archibald is not truly continuous, however, since the sweeps each require a finite period of time to complete and analyze. In practice the sweeps are repeated with minimal delay, one after another, throughout the operation of the device. During applanation mechanism resetting and subsequent sweep operations, the system is effectively "dead" to new data as it analyzes and displays the data obtained during a previous sweep period. This is clearly disadvantageous from the standpoint that significant portions of data are effectively lost, and the operator receives what amounts to only periodic indications of the subject's blood pressure (i.e., one new pressure beat display every 15-40 seconds).

Lastly, the techniques for non-invasive pressure measurement disclosed by the Assignee of the present invention in U.S. Pat. Nos. 6,228,034, 6,176,831, 5,964,711, and 5,848,970, each entitled "Apparatus and method for non-invasively monitoring a subject's arterial blood pressure" and incorporated herein by reference in their entirety, include modulation of applanation level at, inter glia, frequencies higher than the heart rate (e.g., sinusoidal perturbation at 25 Hz). Further, Assignee has determined over time that it is desirable in certain circumstances to control the applanation level according to other modulation schemes and/or frequencies, and/or which are not regular or deterministic in nature, such as those disclosed by co-owned U.S. Pat. No. 6,974,419, entitled "Method and apparatus for control of non-invasive parameter measurements" and incorporated herein by reference in its entirety. Each of the foregoing methods, however, distinguishes between two modes of operation, the first being (1) calibration; and the second being known as (2) patient monitoring mode ("PMM").

"Simulated Annealing"

Simulated annealing (SA) is a term that relates to optimization schema that are related to or modeled generally after physical processes. For example, one branch of simulated annealing theory is a generalization of a Monte Carlo method for examining the equations of state and frozen states of n-body systems. The concept is based to some degree on the manner in which liquids freeze or metals recrystalize during the physical process of annealing. In an annealing process, material initially at high temperature and disordered, is cooled so as to approximately maintain thermodynamic equilibrium. As cooling proceeds, the system becomes more ordered and approaches a "frozen" ground state at Temperature (T)=0. Accordingly, SA can be thought of as analogous to an adiabatic approach to the lowest energy state. If the starting temperature of the system is too low, or the cooling regimen is insufficiently slow, the system may form defects or freeze in meta-stable states; i.e., become trapped in a local minimum energy state.

One scheme (Metropolis) selects an initial state of a thermodynamic system (energy E and temperature T), and holding T constant, the initial configuration is perturbed, and the change in energy (dE) determined. If the change in energy is negative, the new configuration is accepted. If the change in energy is positive, it is accepted with a probability determined by the Boltzmann factor exp–(dE/T). This processes is then repeated sufficient times to give adequate sampling statistics for the current temperature. The temperature is then decremented, and the entire process repeated until a "frozen" state is achieved (at T=0).

This Monte Carlo approach can be analogized to combinatorial problems. The current state of the thermodynamic system is analogous to the current solution to the problem. The energy equation for the thermodynamic system is analogous to the objective function. The ground state is analogous to the global minimum.

A significant difficulty in implementing this algorithm, however, is that there is often no obvious analogy for the temperature (T) with respect to a parameter in the combinatorial problem. Furthermore, avoidance of entrainment in local minima (quenching) is dependent on an "annealing schedule", the choice of initial temperature, the number of iterations performed at each temperature, and how much the temperature is decremented at each step as cooling proceeds.

Based on the foregoing, there is needed an improved apparatus and methodology for accurately and continuously controlling the non-invasive measurement of parameters such as pressure. Such improved methodology and apparatus would ideally integrate the highly efficient simulated annealing (SA) approach and allow for, inter glia, continuous measurement (tonometrically or otherwise) of one or more physiologic or hemodynamic parameters, the measured values of such parameters being reflective of true (e.g., intra-arterial) parameters, while also providing robustness and repeatability under varying environmental conditions including motion artifact and other noise. In addition, such method and apparatus would operate under a substantially unified scheme, as opposed to the two or more independent schemes modeled in prior art devices.

Such a method and apparatus would also be easily utilized by trained medical personnel and untrained individuals, thereby allowing subjects to accurately and reliably conduct self-monitoring if desired.

SUMMARY OF THE INVENTION

In a first aspect of the invention, transient-resistant apparatus for determining the blood pressure of a living subject is disclosed. In one embodiment, this comprises a processor and a computer program running on said processor, said program comprising at least one simulated annealing related algorithm.

In a second aspect of the invention, a method of determining hemodynamic parameters using a simulated annealing-based algorithm is disclosed.

In a third aspect of the invention, a computer storage medium comprising a computer program adapted for substantially unified mode operation according to a simulated annealing algorithm is disclosed.

In a fourth aspect of the invention, a method of maintaining a substantially optimal level of compression for the vessel using dynamically applied dither perturbations on at least one axes associated with the vessel is disclosed.

In a fifth aspect of the invention, a method of treating a living subject based on simulated annealing techniques for assessing hemodynamic parameter(s) is disclosed.

In a sixth aspect of the invention, a method of compensating for transient events so as to maintain a hemodynamic assessment process in a substantially optimal state is disclosed.

In a seventh aspect, a transient-resistant apparatus for determining the blood pressure of a living subject is disclosed. In one embodiment, the apparatus includes: a pressure transducer configured to be disposed proximate a blood vessel of the living subject; and a processor configured to run a computer program thereon, the computer program comprising a plurality of instructions which are configured to, when executed, perform at least one simulated annealing related algorithm to control a placement of the pressure transducer, and to maintain the pressure transducer in an optimized operational state.

In an eighth aspect, a method of determining hemodynamic parameters of a living subject is disclosed. In one embodiment, the method includes: (i) disposing a pressure transducer on the subject, the pressure transducer configured to applanate the subject's tissue and obtain an initial data set of measured pulse pressure; executing a randomly determined trial sequence; (ii) obtaining a second plurality of data regarding measured pulse pressure at least during the act of executing; (iii) processing the second plurality of data; and (iv) adjusting one or more parameters based at least in part on results obtained from the act of processing.

In a ninth aspect, a computer readable apparatus is disclosed. In one embodiment, the apparatus includes a computer program having a plurality of instructions, for the program configured to determine an optimized location for placement of a pressure transducer on a living subject to obtain hemodynamic measurements therefrom. In one variant, the plurality of instructions are configured to, when executed: (i) obtain a first pulse pressure measurement from the pressure transducer at a first location on a skin surface of the living subject; (ii) based at least in part on the pressure measurement, determine a first value indicative of a closeness of the first location to an optimal location; (iii) generate a trial sequence; (iv) direct the pressure transducer to relocate to at least one second location according to the trial sequence; (v) obtain pressure measurements from the pressure transducer at the at least one second location; and (vi) based at least in part on the pressure measurements obtained, determine a second value, the second value being indicative of a closeness of the at least one second location to the optimal location.

In a tenth aspect, a method of maintaining a substantially optimal level of compression of a blood vessel of a living subject using dynamically applied dither perturbations on at least one axes associated with the blood vessel is disclosed. In one embodiment, the method includes: (i) generating an average of continuously obtained hemodynamic measurements via at least one pressure transducer, the measurements being measured at an optimal level of compression of the blood vessel by the pressure transducer; (ii) receiving at least one hemodynamic measurement which is at least a predetermined amount outside of the average; (iii) applying a random dither to the pressure transducer; (iv) obtaining pressure measurements from the pressure transducer at least after the application of the dither; and (v) based at least in part on the pressure measurements obtained at least after the dither, determining whether the optimal level of compression has been re-established.

These and other features of the invention will become apparent from the following description of the invention, taken in conjunction with the accompanying drawings.

BRIEF DESCRIPTION OF THE DRAWINGS

FIG. 4d is a graph illustrating transition probabilities as a function of pulse pressure and temperature in accordance with one embodiment of the present invention.

DETAILED DESCRIPTION OF THE INVENTION

Figure 1:
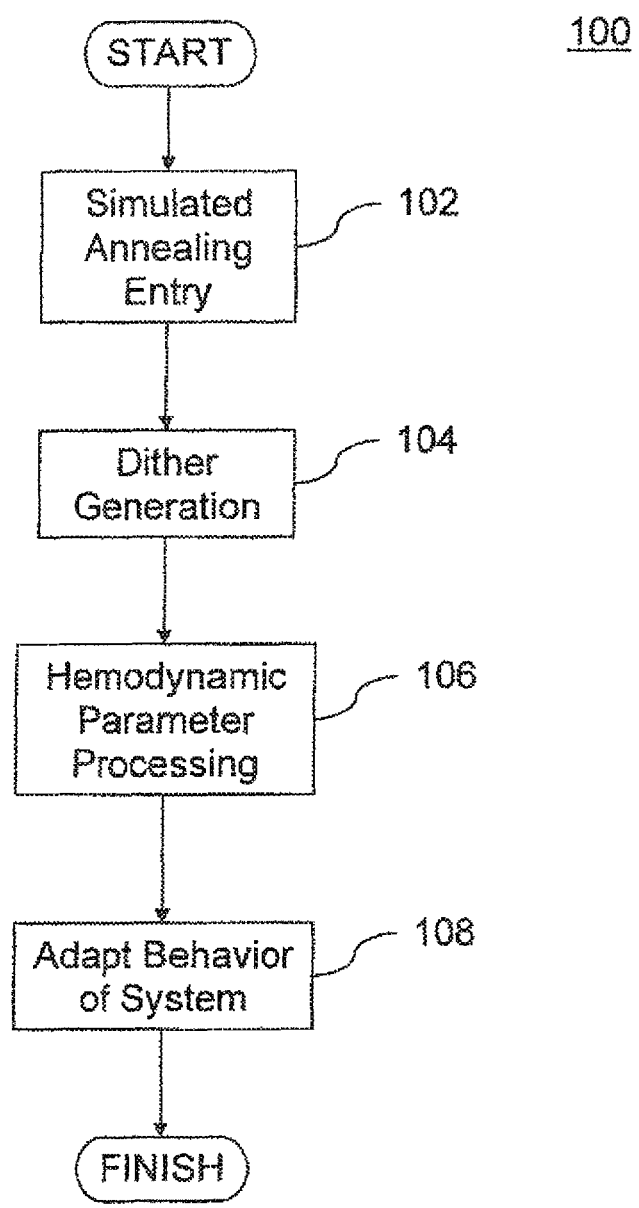
FIG. 1 is a flow diagram illustrating the fundamental process steps performed in accordance with one exemplary embodiment of the control methodology of the present invention.

Reference is now made to the drawings wherein like numerals refer to like parts throughout.

It is noted that while the invention is described herein primarily in terms of a apparatus and methods for the control of non-invasive measurements of hemodynamic parameters such as blood pressure obtained via the radial artery (i.e., wrist) of a human subject, the invention may also be readily embodied or adapted to monitor such parameters at other blood vessels and locations on the human body, as well as monitoring these parameters on other warm-blooded species. Similarly, the techniques of the present invention can be applied to other parameters, as well as other similar fluidic systems which have similar properties to those of the circulatory system of a living being. All such adaptations and alternate embodiments are readily implemented by those of ordinary skill in the relevant arts, and are considered to fall within the scope of the claims appended hereto.

As used herein, the term "continuous" is meant to include without limitation continuous, piece-wise continuous, and/or substantially continuous processes (e.g., those which are generally continuous in nature, but are not per se continuous).

As used herein, the term "hemodynamic parameter" is meant to include parameters associated with the circulatory system of the subject, including for example pressure (e.g., diastolic, systolic, pulse, or mean pressure), derivatives or combinations thereof, arterial flow, arterial wall diameter (and its derivatives), cross sectional area of the artery, and arterial compliance.

Additionally, it is noted that the terms "tonometric," "tonometer," and "tonometry" as used herein are intended to broadly refer to non-invasive surface measurement of one or more hemodynamic parameters, such as by placing a sensor in communication with the surface of the skin, although contact with the skin need not be direct, and can be indirect (e.g., such as through a coupling medium or other interface).

The terms "applanate" and "applanation" as used herein refer to, without limitation, the compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other forms, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"; or (vi) a deterministic profile. All such forms are considered to be encompassed by these terms.

As used herein, the term "epoch" refers to any increment of time, ranging in duration from the smallest measurable fraction of a second to more than one second.

As used herein, the terms "spatial" and "position", although described in terms of a substantially Cartesian coordinate system having applanation (i.e., Z-axis), lateral (X-axis) and (Proximal refers to closer to the heart) longitudinal or (proximal—distal) (Y-axis) components, shall refer to any spatial coordinate system including, without limitation, cylindrical, spherical, and polar. Such use of alternate coordinate systems may clearly be independent of any particular hardware configuration or geometry (e.g., by performing simple mathematical translations between a Cartesian-based apparatus and the non-Cartesian coordinate system), or alternatively make advantageous use of such geometries. The present invention is therefore in no way limited to certain coordinate systems of apparatus configurations. As one example, it will be recognized that the methods and apparatus of the present invention may be embodied using a cylindrical coordinate system modeled around the radial artery, such that a particular point in space for the tonometric sensor(s) can be specified by the Z, r, and θ parameters. This approach may have advantages since the forearm/wrist area of the human being very roughly comprises a cylindrical form.

As used herein, the term "temperature" refers to, without limitation, any parameter which can be correlated or analogized to temperature in an actual or physical annealing process including, for example, confidence level. Temperature as used in the context of the SA models disclosed herein is merely an abstract concept representative of a quantity or property associated with the system being controlled or modeled.

As used herein, the term "application" (in the context of a software application) refers generally to a unit of executable software that implements a certain functionality or theme. The themes of applications vary broadly across any number of disciplines and functions (such as on-demand content management, e-commerce transactions, brokerage transactions, home entertainment, calculator etc.), and one application may have more than one theme. The unit of executable software generally runs in a predetermined environment; for example, the unit could comprise a downloadable Java Xlet™ that runs within the JavaTV™ environment.

As used herein, the term "computer program" or "software" is meant to include any sequence or human or machine cognizable steps which perform a function. Such program may be rendered in virtually any programming language or environment including, for example, C/C++, Fortran, COBOL, PASCAL, assembly language, markup languages (e.g., HTML, SGML, XML, VoXML), and the like, as well as object-oriented environments such as the Common Object Request Broker Architecture (CORBA), Java™ (including J2ME, Java Beans, etc.) and the like.

As used herein, the term "integrated circuit (IC)" refers to any type of device having any level of integration (including without limitation ULSI, VLSI, and LSI) and irrespective of process or base materials (including, without limitation Si, SiGe, CMOS and GaAs). ICs may include, for example, memory devices (e.g., DRAM, SRAM, DDRAM, EEPROM/Flash, ROM), digital processors, SoC devices, FPGAs, ASICs, ADCs, DACs, transceivers, memory controllers, and other devices, as well as any combinations thereof.

As used herein, the term, "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

As used herein, the terms processor. "microprocessor" and "digital processor" are meant generally to include all types of digital processing devices including, without limitation, digital signal processors (DSPs), reduced instruction set computers (RISC), general-purpose (CISC) processors, microprocessors, gate arrays (e.g., FPGAs), PLDs, reconfigurable compute fabrics (RCFs), array processors, and application-specific integrated circuits (ASICs). Such digital processors may be contained on a single unitary IC die, or distributed across multiple components.

Overview

In one fundamental aspect, the present invention comprises apparatus and methods for controlling an applanation or other positioning mechanism used in physiologic analysis such as, e.g., non-invasive hemodynamic parameter measurements in order to, inter alia, maintain optimal coupling between a parameter sensor and the blood vessel of interest. These improved apparatus and methods are based on simulated annealing (SA) paradigms that provide a substantially unified and highly effective means for placing and maintaining the hemodynamic assessment or other such system in an optimized operational state. Maintenance of this state correlates, inter alia, to the best possible accuracy for the parameter(s) (e.g., blood pressure) being measured.

Exemplary techniques for determining the optimal applanation level, position, and coupling that can be utilized with or benefit from the present invention are described in detail in, e.g., co-owned U.S. Pat. No. 6,730,038 entitled "Method And Apparatus For Non-Invasively Measuring Hemodynamic Parameters Using Parametrics" issued May 4, 2004 and co-owned U.S. Pat. No. 6,974,419 entitled "Method and Apparatus for Control of Non-Invasive Parameter Measurements" issued Dec. 13, 2005 each of which are incorporated by reference herein in their entirety.

The improved techniques and apparatus of the present invention advantageously may be used with a broad range of hardware configurations, including e.g., a single sensor (or array of sensors) as described in detail herein and the aforementioned and incorporated applications, or in conjunction with literally any type of other apparatus adapted for hemodynamic parameter measurement, including for example the devices described in U.S. patent application Ser. No. 09/815, 982 entitled "Method and Apparatus for the Noninvasive Assessment of Hemodynamic Parameters Including Blood Vessel Location" filed on Mar. 22, 2001 and patented as U.S. Pat. No. 7,503,896 on Mar. 17, 2009, and U.S. patent application Ser. No. 09/815,080 entitled "Method and Apparatus for Assessing Hemodynamic Parameters within the Circulatory System of a Living Subject" also filed on Mar. 22, 2001 and patented as U.S. Pat. No. 7,048,691 on May 23, 2006, both of which are assigned to the assignee hereof and incorporated herein by reference in their entirety. For example, an entirely tonometric pressure-based approach can be used. Alternatively, ultrasound measurements of blood pressure via blood flow kinetic energy or velocity can be used as a confirmatory technique for the tonometric pressure-based approach. As another example, lateral positioning based on analysis of the acoustic signals relating to vessel wall detection may be used in addition to (or in place of) the pressure-based techniques described in the cited co-owned patents and patent applications.

Hence, the various aspects of the present invention are advantageously compatible with a number of different physiologic and hemodynamic assessment techniques. It will also be recognized that the techniques and apparatus described herein are in no way limited to tonometric applications; rather, these features may be implemented even in e.g., occlusive cuff or pellot-based systems.

While the techniques described in the aforementioned co-pending patent and patent applications have been determined by Assignee to be highly effective, their robustness and utility in practical (e.g., clinical) settings is enhanced through the addition of one or more of the various aspects of the present invention. In the context of blood pressure measurement, existing approaches to acquire and measure the patient's mean arterial blood pressure focused on the compression of the patient's tissues at a location directly over their artery of interest (e.g., the radial artery) such that the observed pulse pressure was maximized. It is at this point of maximum pulse pressure that the pressure exerted on the compressed artery equals the mean arterial pressure. Observance of the mean arterial pressure in an accurate way was largely predicated on locating the artery correctly, and compressing the artery at an appropriate level of applanation.

Under some such approaches, location of the artery was accomplished using two discrete steps or phases. First during an initial calibration phase, a scan of a narrow portion of an acquisition space is performed by making broad movements along both the lateral and applanation axes. Second, during the second phase of operation, the applanation location is fine tuned using a series of small experimental dithers around the current operating point located during the calibration phase. In this way, the two phases of artery location and applanation can be viewed as a "large signal experiment" followed by a "small signal experiment".

While there normally is no sense that a large signal experiment is better or worse than a small signal experiment, there are some issues introduced to the system under measurement by implementing such an approach. First, the observed pulse pressure may not only be a function of the actual position of the transducer with respect to the artery, but it quite probably is also a function of the history of stresses placed upon the involved tissues by the actuator. It would therefore be reasonable to expect that this historical effect may be amplified with larger disturbances of the system seen during initial calibration.

Second, using two separate modes of operation assumes that the system (i.e. the transducer, actuator and patient's tissues) will respond similarly during both large signal and small signal experiments, in effect assuming the system behaves in a linear fashion. However, the operating point located during the initial calibration phase and the operating point located during the second phase may be two different "answers" that are only appropriate to their own respective phases of operation. In systems where only small adjustments are made to the applanation position and the lateral position subsequent to calibration, such a two phase solution can be problematic as the operating point located during calibration may not be the ideal operating point location for the second phase and the control system can have a tendency to get stuck at a local, as opposed to global, maxima.

Therefore in accordance with one embodiment of the invention, a method and apparatus are provided for monitoring hemodynamic parameters, such as blood pressure, in a continuous and non-invasive manner while operating under a single unifying scheme. In a sense, this approach acknowledges the fact that we are constantly calibrating, always questioning whether or not we are at the patient's optimal operating point to measure the hemodynamic parameter of interest. One embodiment of the invention includes a measurement apparatus for measuring various hemodynamic parameters associated with the human body. In addition, a digital processor is disclosed for calculating various parameters in response to the measured parameters. Additionally, the invention includes a method and apparatus for controlling the location of the measurement in response to information generated by the digital processor.

In accordance with a described embodiment of the hemodynamic system monitoring apparatus, the hemodynamic system apparatus implements a "simulated annealing" process which unifies measurements under a single scheme of operation. In one exemplary embodiment of the simulated annealing process, dithers of varying sizes will be dynamically applied to the system around a given operating point. The size of these dithers will be correlated to a confidence analysis (e.g. so-called temperature measurement), such that larger changes to dither will be applied when confidence is low while smaller more subtle changes will be used when confidence is high. This simulated annealing process will be more resilient against being trapped by so-called local maxima over prior art techniques, as well as being more resilient against varying topologies of hemodynamic parameter curves. This approach also opens up the solution space to the maximum amount allowed by the physical actuator implemented (i.e. by allowing for adjustment in the applanation, lateral and distal axes either serially or in parallel) and by further allowing for dynamic adjustment of the position of the transducer over the radial artery further improving the reliability and robustness of these classes of non-invasive hemodynamic parameter monitors. Further, because the unifying scheme is largely a "small signal" approach, although not necessarily so due to factors such as the aforementioned optimal positioning confidence level, disruptions to the system causing inaccurate non-invasive readings are effectively minimized.

Continuous Positioning Methodology

It will also be recognized that while the process of the present invention is described subsequently herein with respect to a tonometric pressure sensor or transducer, it can be applied more generally to other signal domains including without limitation ultrasonics and electromagnetic radiation (e.g., IR, X-ray, etc.).

Furthermore, it will be appreciated that while primarily described in the context of the aforementioned tonometric apparatus (i.e., a tonometric pressure sensor which also acts to provide varying levels of compression of the underlying tissue and blood vessel(s)), the methodology of the present invention may be practiced using apparatus having separate components which provide these functions. For example, the control of the pressure sensor may be partly or completely decoupled from the applanation control system, such that the level of applanation can be varied independently from the coupling of the active surface(s) of the sensor. A detailed discussion of exemplary electronic and signal processing apparatus used to support the operation of the processes described herein is provided with respect to FIG. 6 below.

It will be recognized by those of ordinary skill that the logical processes of the present invention may also be practiced entirely algorithmically (e.g., in software) and/or firmware.

FIG. 1 is a flow chart illustrating the general control methodology performed to determine, e.g., the hemodynamic parameter(s) (blood pressure, etc.) of a living subject in accordance with one embodiment of the present invention. The overall process can be thought of as constituting four (4) basic methodological steps. The first step 102 comprises the step of entry into the "simulated annealing" process and the pre-requisite calculations for the steps that follow. This first step 102 is described further in detail with regards to FIG. 2 and its accompanying disclosure.

It will be appreciated that the term "simulated annealing" as used herein is merely used as an analogy for sake of easier understanding of the concepts of the invention, and in no way carries any specific connotation or meaning.

In step 104, the variation (e.g., dither) generation process is initiated. The set of dither factors typically includes an applanation dither factor, a lateral dither factor and a distal dither factor, corresponding to the applanation, lateral and distal axes respectively for the measuring apparatus. The dither generation process is discussed further herein with regards to FIG. 3 and its accompanying disclosure. Alternative embodiments of the invention described herein may include more or less dither factors and/or axes of interest and implementation would be readily apparent to one of ordinary skill given the present disclosure herein.

Step 106 corresponds to the pressure signal processing methodology utilized with regards to the present embodiment of the invention. This methodology is described in further detail with and in part with regards to FIG. 4 and its accompanying disclosure.

In step 108, the system behavior is adjusted based on the aforementioned dither generation and hemodynamic parameter processing steps. Generally speaking, as the confidence level of being located at the optimal point decreases the dither factors utilized are increased in order to allow for "larger" searches of the optimal positioning point, this optimal point being the ideal location from which to obtain hemodynamic parameter readings. Conversely, as the confidence level increases, the dither factor is decreased in order to allow only "smaller" searches for the optimal point in order to obtain hemodynamic parameter readings, while simultaneously minimizing adverse influences on the system as a result of the non-invasive measurement. This adaptive behavior is discussed further with regards to FIG. 5 and its accompanying disclosure.

At this point, the process 100 may end or alternatively the process may continue by performing a new measurement at 102 and repeating one or more of the aforementioned processes. For purposes of simplicity and brevity, processes 102, 104, 106 and 108 will be primarily discussed with regards to only two axes of interest (i.e., applanation and lateral), although it is recognized that more or less axes processing steps could be implemented consistent with the principles of the present invention.

(1) Simulated Annealing Entry

Figure 2:
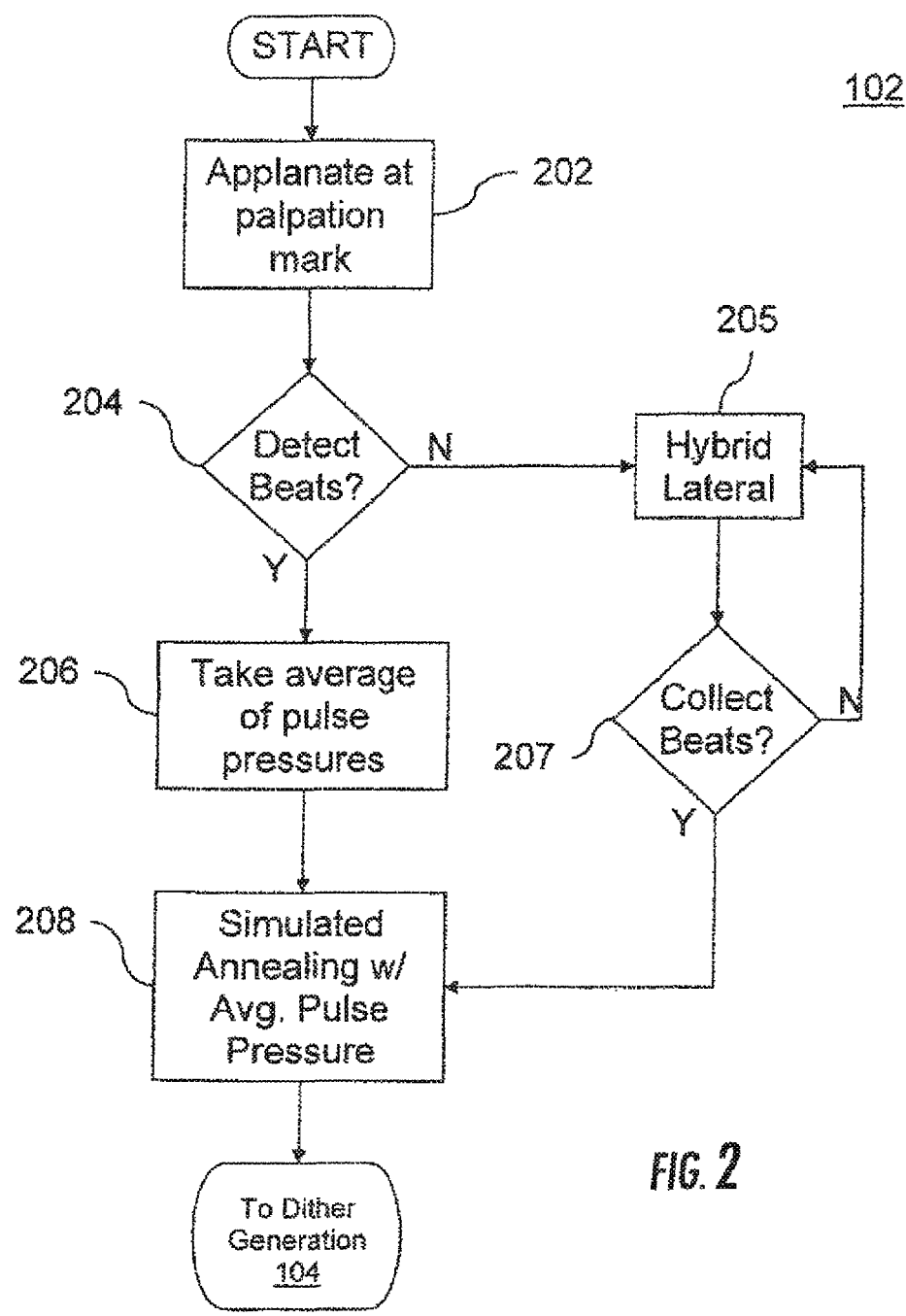
FIG. 2 is a flow diagram illustrating the operation of the exemplary embodiment of the first (annealing entry) process of FIG. 1.

Referring now to FIG. 2, one exemplary embodiment of the simulated annealing entry process 102 is shown. While the exemplary simulated annealing process is described in conjunction with the use of tonometric blood pressure monitoring system, such as for example the TL-150 developed and marketed by Tensys® Medical, Inc., the invention is in no way so limited. In fact, the process discussed with regards to FIG. 2 may be utilized within the framework of a plurality of different apparatus measuring other physiologic or hemodynamic parameters, the aforementioned TL-150 merely being exemplary.

In step 202, a pressure transducer is applanated along the applanation axis at a desired location; e.g., a palpation mark determined by a user, or location determined via vessel location mechanism or technique such as ultrasound or the like. In a first embodiment, the palpation mark is determined manually by first, palpating the radial styloid process and then drawing a transverse line over this bone. Next, the location of the patient's pulse is determined and the user will draw a line perpendicular to and intersecting the transverse line previously drawn. The intersection of this line will be referred to herein as the palpation mark. While discussed in terms of locating along the radial styloid process on a patient's wrist, the palpation technique described herein could be equally applicable to other areas of the human body, such as e.g. the ulnar pulse point, carotid pulse point, or brachial pulse point, etc. The measuring apparatus is then placed over the palpation mark and the pressure transducer will applanate the patient's tissue at the palpation mark to a specified applanation pressure (such as e.g. 85 mm-Hg).

In step 204, it is determined whether the apparatus can detect pulse beats originating from the pulse point (e.g., the radial pulse point palpation mark). If a pulse is detected, then the apparatus will take an average of the pulse pressures observed over a specified number of beats (e.g. four (4)), or employ another scheme for obtaining a desired data set at step 206, and the process will then invoke the simulated annealing process with average pulse pressure measurements at step 208. If the pulse is not detected, then a "hybrid" lateral process step is invoked at step 205.

Assuming that a pulse beat has not been detected, the hybrid lateral processing step is invoked at step 205. Here, the apparatus will begin looking for beats by performing a lateral scan beginning at a point that is a specified distance from the beginning of possible lateral travel. It has been found through experiment that the specified distance of travel from the beginning of possible lateral travel is often most effective at approximately ¼ of an inch (0.25 in.), although more or less travel clearly may be utilized.

Next, the apparatus will "servo" (i.e., continuously or semi-continuously vary) the applanation position in order to maintain an average pressure at a specified position such as e.g. 60 mm-Hg. During the lateral scan, any beats collected by the apparatus are noted along with the position and pressure reading of the sensor at the time of detection.

At this point in the hybrid lateral process, the apparatus determines whether it has collected a predetermined number of beats (e.g. four (4) in the illustrated embodiment), or has reached the end of lateral travel without detecting the required number of beats. If the end of the specified lateral travel has been reached without detecting the specified number of beats, step 205 is repeated; however this time a lower lateral scan velocity is used, and/or the possible lateral travel area is increased.

On the other hand, if the predetermined number of beats had been collected, the transducer will be positioned over the lateral position as indicated by the largest reading of the collected beats. At the point, the apparatus will servo the applanation position of the transducer until an average desired pressure (e.g., 85 mm-Hg) is reached, and collect another predetermined number of beats in step 207.

In step 207, if it is determined the hybrid lateral process of step 205 was entered into as a result of a motion recovery process; then the number of beats collected will be specified at a number such as e.g. twenty (20) collected beats. If not a result of a motion recovery process, a fewer number of collected beats is needed, such as e.g. four (4) beats. The apparatus will then either query whether the required number of beats have been collected in a specified time limit, and if the apparatus returns "true" to this inquiry, the apparatus will average the pulse pressure measurements collected over the collected number of beats and invoke step 208, the simulated annealing process.

If the apparatus times out prior to collecting the specified number of beats, then the hybrid lateral process will repeat, but with a lower scan velocity. If this repeated hybrid lateral process is repeated over a predetermined number of times (e.g. two (2)), then the user will be notified of the processing error, and the process will be terminated or a diagnostic or troubleshooting mode entered if desired.

Figure 2A:
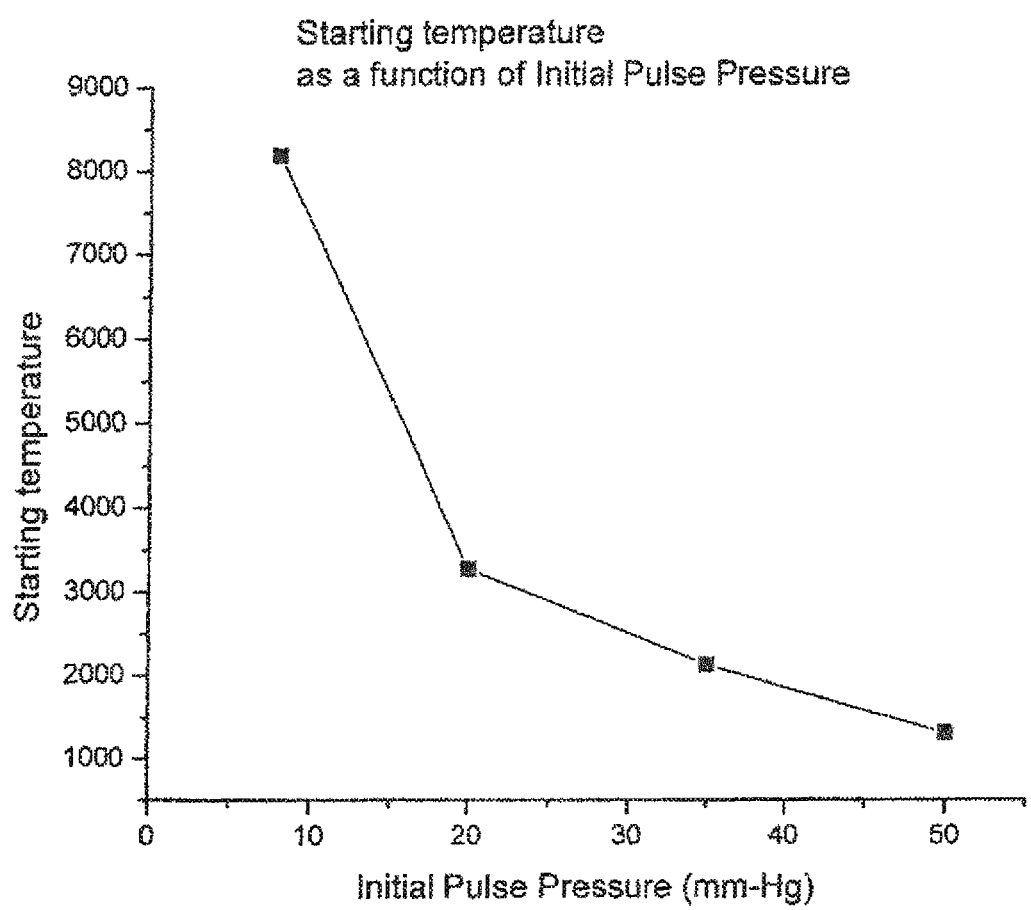
FIG. 2a is a graph illustrating starting system temperature as a function of initial pulse pressure for one exemplary embodiment of the present invention.

In step 208, the simulated annealing process is invoked tointer alia prepare for entry into subsequent dither generation processing steps, as described further below with regards to FIG. 3 and its accompanying disclosure. A starting temperature value is selected in step 208 using the chart of FIG. 2a showing starting temperature as a function of initial pulse pressure. FIG. 2a demonstrates the functional relationship between starting temperature (relative units) selected versus initial pulse pressure (in mm-Hg). For purposes of hardware simplicity, a 1-D interpolator may be used to perform a piecewise linear interpolation of the starting temperature versus initial pulse pressure chart of FIG. 2a during step 208, although more complex interpolations, or curve fitting algorithms are possible such as e.g. polynomial or even spline interpolation.

(2) Dither Generation

Figure 3:
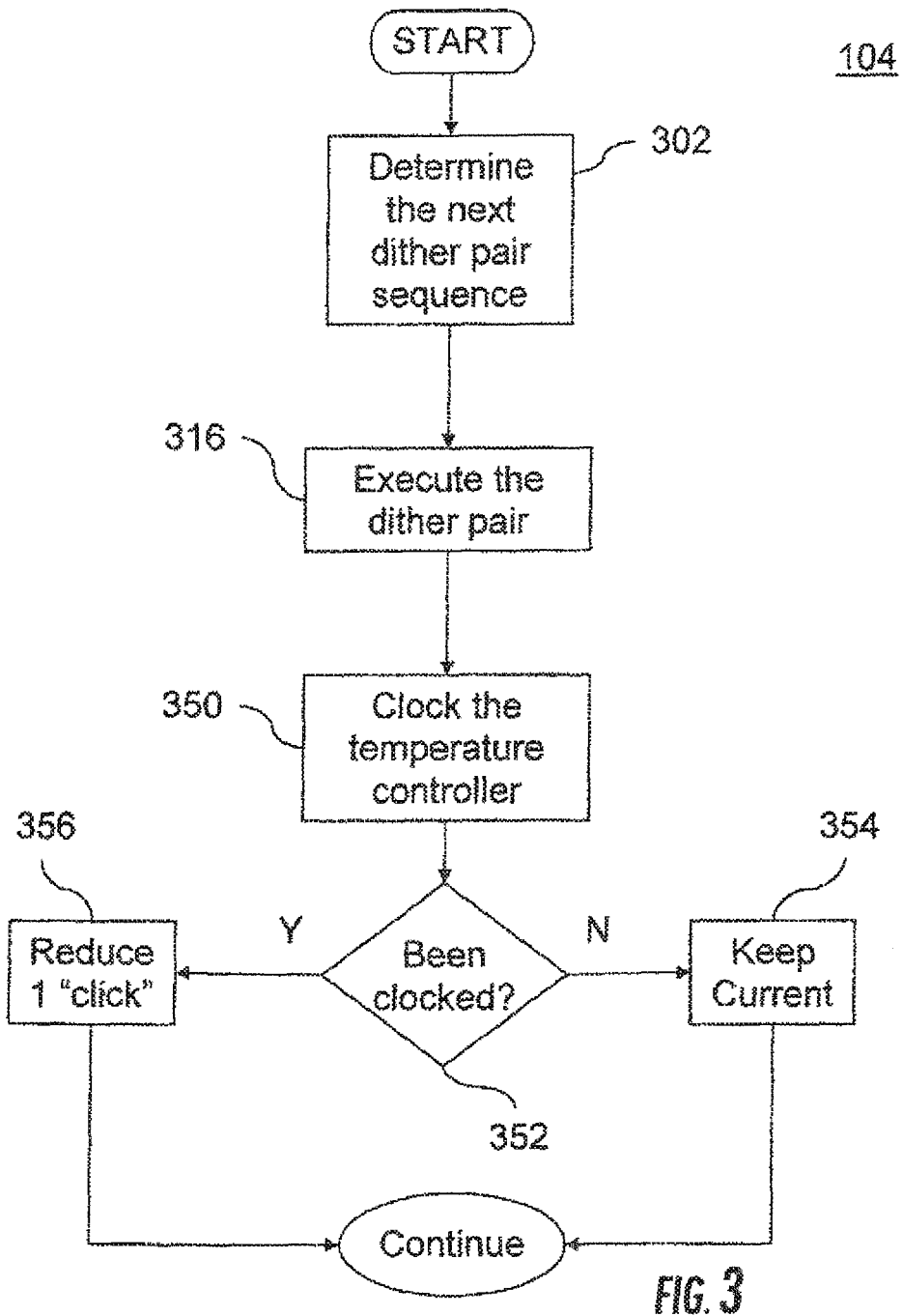
FIG. 3 is a flow diagram illustrating the operation of one exemplary embodiment of the second process (dither generation) of FIG. 1.

Referring now to FIG. 3, one exemplary method for dither generation 104 is discussed in detail. At a high level, the exemplary dither generation process 104 involves three basic steps of operation: (1) determination of the next dither pair sequence 302; (2) execution of the dither pair 316; and (3) clocking the temperature controller 350 according to a pre-specified scheme.

Regarding steps (1) and (2), i.e. dither pair determination and execution, these processing steps will be discussed in detail below with regards to FIGS. 3a, 3b and 3c.

Regarding step (3), logic within the apparatus will determine whether the temperature controller has been clocked a pre-specified (e.g. two (2)) number of times at step 352. If the logic returns "true", the current temperature will be reduced by by a prescribed amount; e.g., one "click", at step 356. If the logic returns false, the current temperature will be maintained at step 354.

Figure 3A:
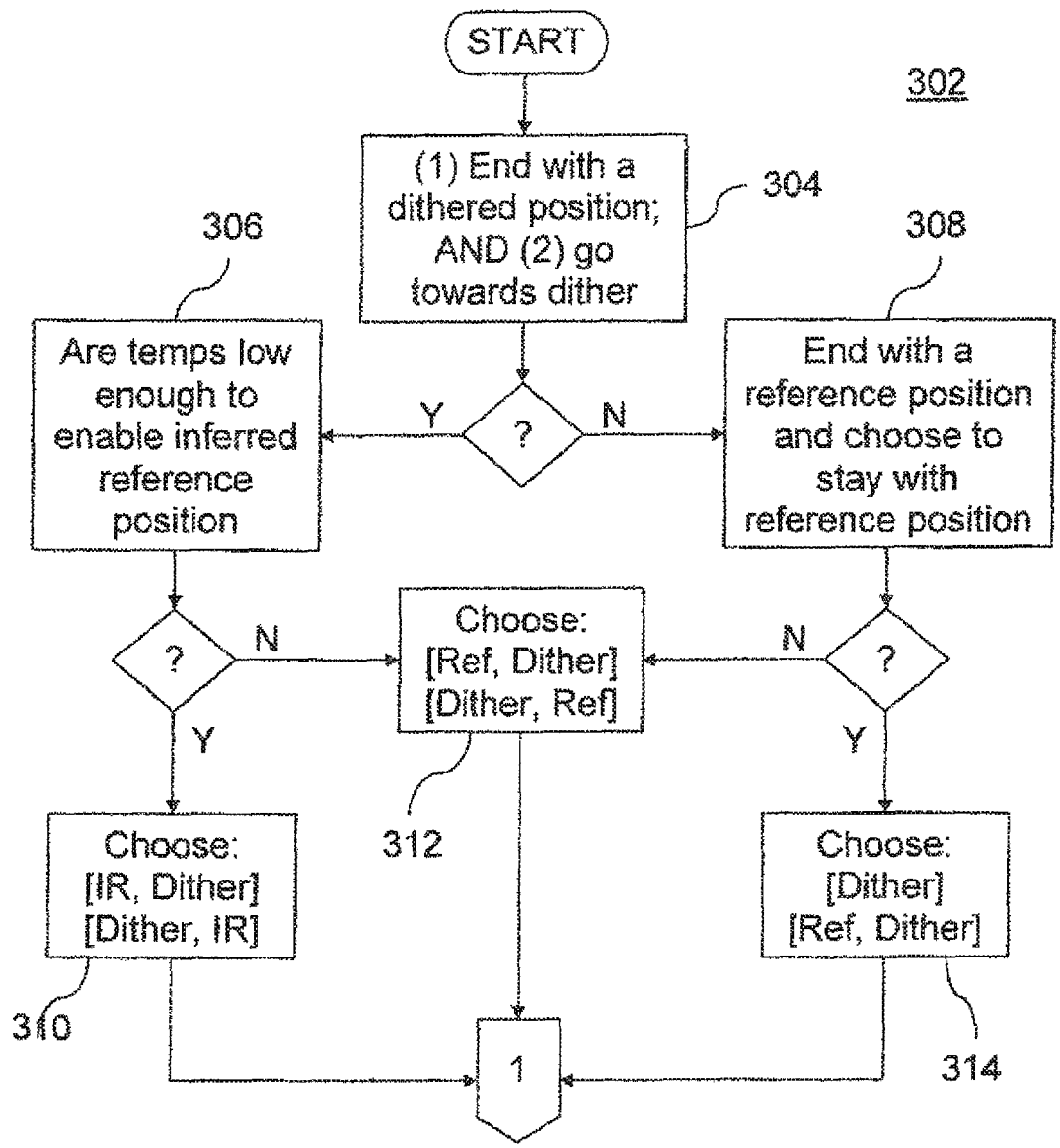
FIG. 3a is a flow diagram illustrating one exemplary process flow for determining the next dither pair sequence and executing the dither pair of FIG. 3.
Figure 3A:
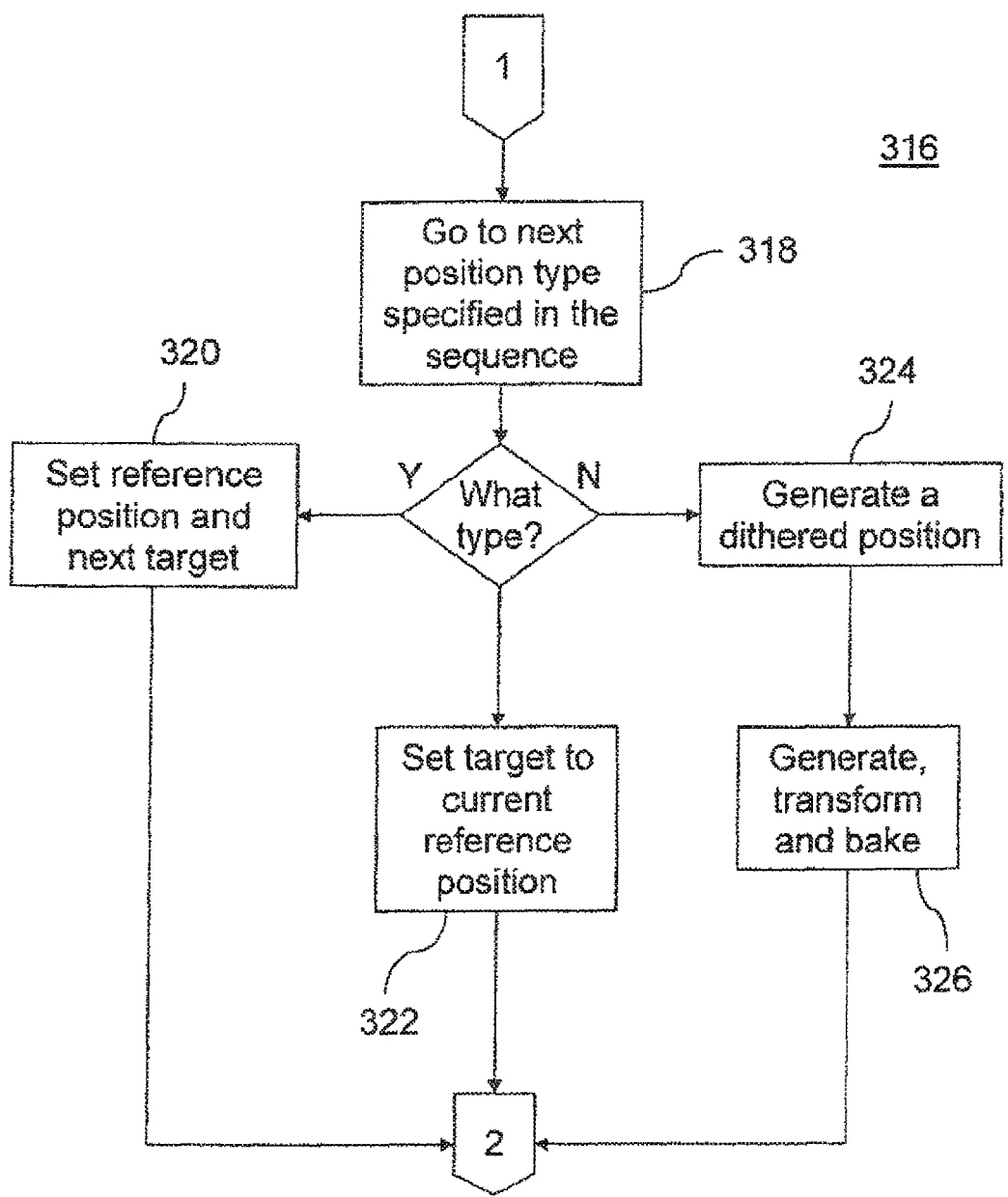
Figure 3A:
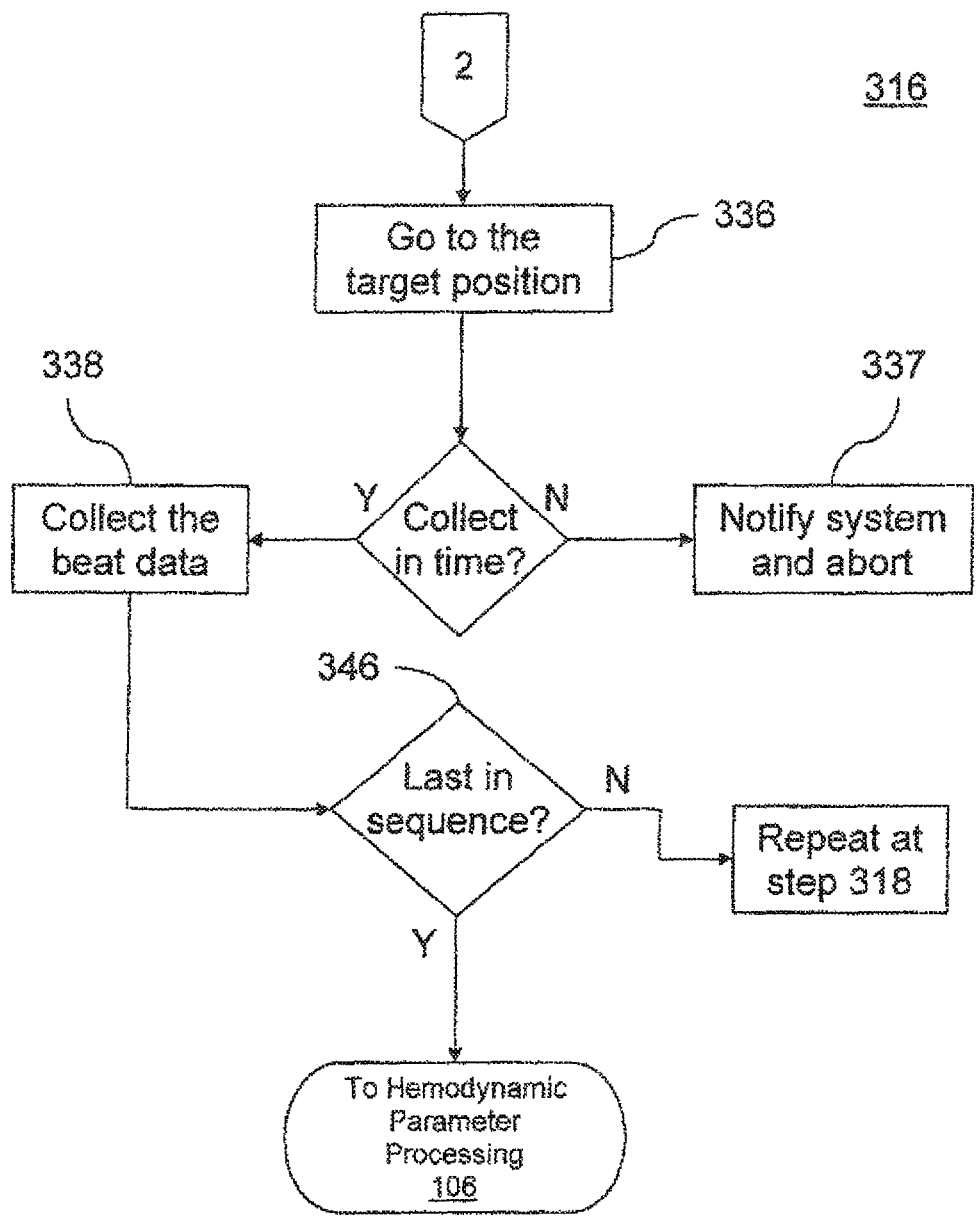

Referring now to FIG. 3a, an exemplary embodiment of the process for determining the next dither pair sequence 302 is described in detail. A dither pair sequence determines the order of "experiments" or trials used when evaluating two different positions for the transducer apparatus. A dither pair sequence can thus be thought of as the center, or "heart" of the simulated annealing process that controls the positioning of the transducer under this unifying scheme.

In the present embodiment, the dither pair sequence is substantially randomized. The reasoning for this can perhaps best be explained by example. For instance, imagine that activity with regards to the patient's pulse pressure is in reality uncorrelated with the apparatus movements. If this activity involves monotonic changes over large periods of time, such as a result of a particular physiological or pharmacological effect, fixing the order of the "experiments" or trials will have a very predictable and undesirable influence on the test results. For example, in cases where the patient's pulse pressures are monotonically increasing, and this increase is such that it is stronger than any influence exerted by moving the transducer position, then whichever position tested last in the dither pair will usually dominate, given that it will have the higher observed pulse pressure (as we are monotonically increasing in pressure). In such a case the transducer position would almost never move away from the previously established position. Conversely, if always ending with the dithered position last in each dither pair, the transducer position would always tend to move away with each dither pair to the randomly chosen dither. In order to combat this effect, the order of the dither pair is randomized, effectively eliminating any long-term accidental and non-causal correlation with external pulse pressure changes. Other schemes may be used to avoid such effects as well, however, including those which specifically analyze the possible effects (such as the foregoing monotonic scenario) and adaptively develop a scheme which combats or mitigates such deleterious effects. Furthermore, randomization may not be required at all times, and hence may be applied selectively if desired.

As is known in the mathematical arts, randomizing of signals and/or numerical sequences is most typically implemented through the use of so called pseudo random number generators which generate Pseudo Random Binary Sequences (PRBS). Pseudo Random Binary Sequences (PRBS) are a defined sequence of inputs (+1/−1) that possess correlative properties similar to white noise, but converge in within a give time period. In addition, the inputs can be specified (and thereby optimized) to produce more effective signal-to-noise ratio (SNR) within the constraints of the system. One common type of PRBS sequence generator uses an n-bit shift register with a feedback structure containing modulo-2 adders (i.e. XOR gates) and connected to appropriate taps on the shift register. The generator generates a maximal length binary sequence according to Eqn. 1:

$$\text{maximal length binary sequence} = \text{length}(2^n - 1) \quad \text{(Eqn. 1)}$$

The maximal length (or "m-sequence") has nearly random properties that are particularly useful in the present invention, and is classed as a pseudo-noise (PN) sequence. Properties of m-sequences commonly include:

(a) "Balance" Property—For each period of the sequence, the number of '1's and '0's differ by at most one. For example in a 63 bit sequence, there are 32 '1's and 31 '0's.

(b) "Run Proportionality" Property—In the sequences of '1's and of '0's in each period, one half the runs of each kind are of length one, one quarter are of length two, one eighth are of length three, and so forth.

(c) "Shift and add" Property—The modulo-2 sum of an m-sequence and any cyclic shift of the same sequence results in a third cyclic shift of the same sequence.

(d) "Correlation" Property—When a full period of the sequence is compared in term-by-term fashion with any cyclic shift of itself, the number differences is equal to the number of similarities plus one (1).

(e) "Spectral" Properties—The m-sequence is periodic, and therefore the spectrum consists of a sequence of equally-spaced harmonics where the spacing is the reciprocal of the period. With the exception of the dc harmonic, the magnitudes of the harmonics are equal. Aside from the spectral lines, the frequency spectrum of a maximum length sequence is similar to that of a random sequence.

In step 304, the apparatus will first determine whether in the previous dither pair, did the apparatus both: (1) end with a dithered position; and (2) choose to go towards the dither. In other words, was a new reference position established with the dithered position last. If so, then step 306 is invoked, Conversely, if the answer is no, then step 308 is invoked.

Assuming for a moment, that the answer to the logical query of step 304 was yes, then step 306 is invoked. At step 306, the apparatus queries to determine whether the temperature (i.e. the starting temperature selected at step 208) is low enough to enable an inferred reference position. An inferred reference position, as opposed to a standard reference position, is a position that can be extrapolated upon a very specific circumstance. This inferred reference position is extrapolated when a new dithered position is tested and the apparatus, and the underlying algorithm, decides to go towards this new dithered position.

A new reference position, at a predetermined distance between the two points beyond the dithered position in a direction that is further away from the previous reference position is "inferred". In one exemplary embodiment, this predetermined distance is $\frac{1}{3}^{rd}$ (33.333%) of the previous dither. This in effect exaggerates the original dither movement by an additional $\frac{1}{3}^{rd}$ of the previous dither. However, such exaggerations are typically only deployed at low temperatures to avoid excessive movements. At low temperatures this extrapolation is desirable, as it provides a quantity of gain in order to increase slew rate beyond that which a given dither size would otherwise imply.

Figure 3B:
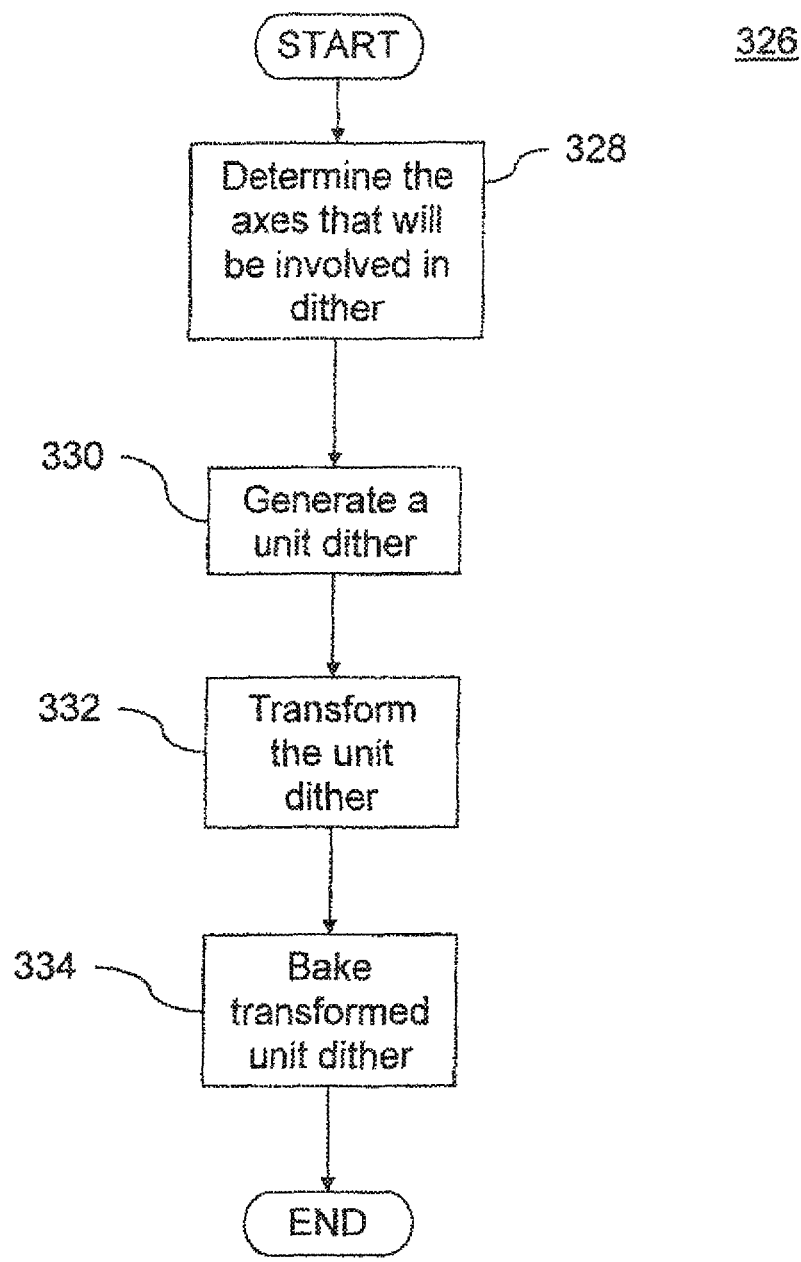
FIG. 3b is a flow diagram illustrating one exemplary process flow for generating, transforming and baking a unit dither according to one embodiment of the present invention.
Figure 3C:
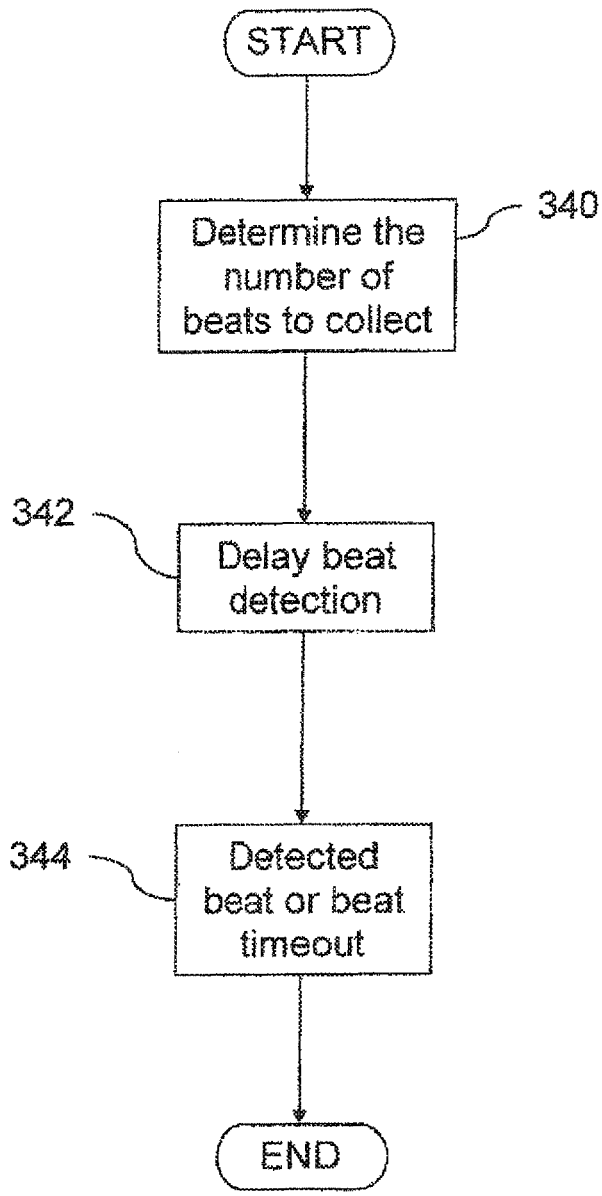
FIG. 3c is a flow diagram illustrating one exemplary process flow for collecting beat data in accordance with one embodiment of the present invention.
Figure 3D:
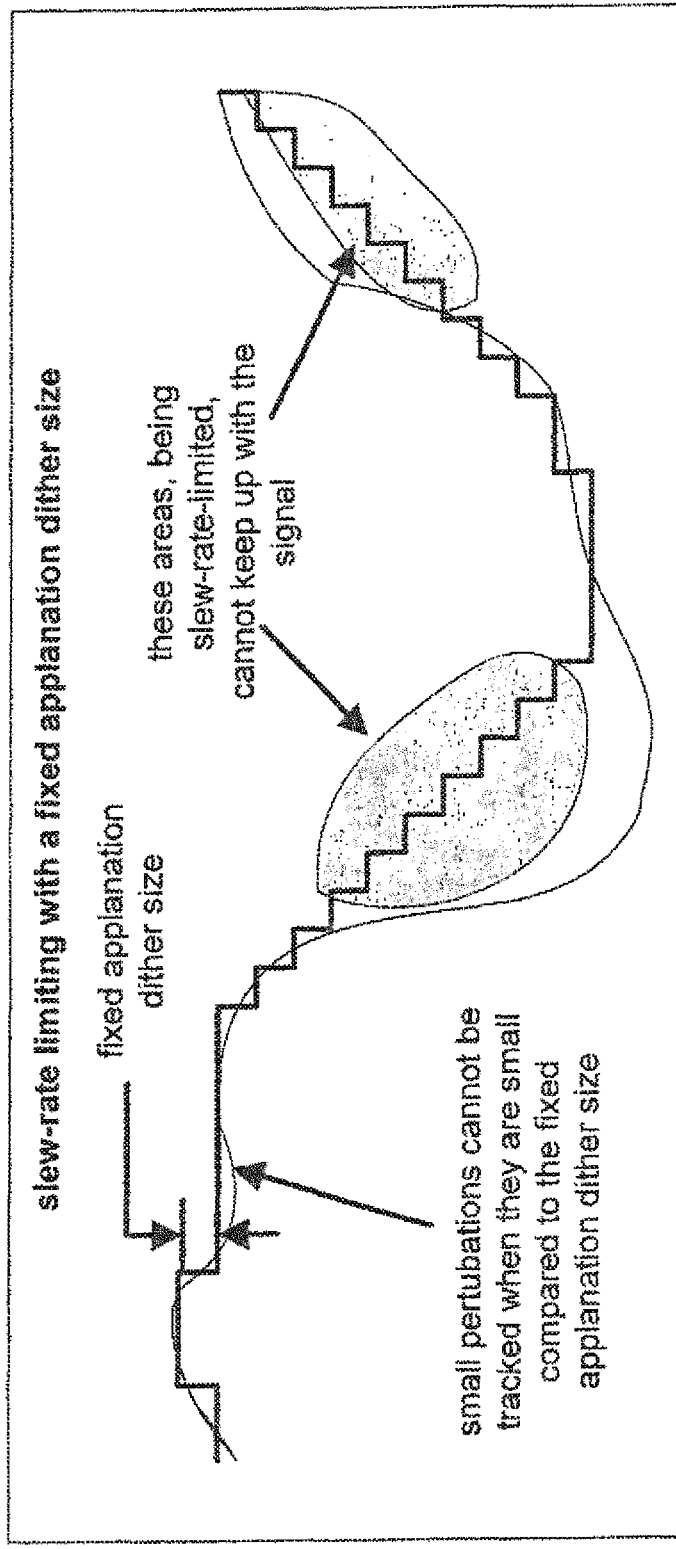
FIG. 3d is a graph illustrating the drawbacks of fixed applanation dither size as it applies to slew-rate limiting in accordance with the principles of the present invention.

FIG. 3d graphically demonstrates for the utility of the aforementioned concept. Specifically, in cases where there is a fixed applanation dither size, small perturbations cannot be tracked when they are small compared to the fixed applanation dither size. Further, with large variations in the hemodynamic parameter measured, fixed applanation dither sizes may have difficulty in keeping up (i.e. because they are typically slew-rate-limited) with the signal. Therefore, as can be seen in FIG. 3d, it would be desirable to vary the dither size as a function of confidence (i.e. by lowering dither size to measure small perturbations when confidence is high and exaggerating dither size when confidence is low as a result of large variations in the signal).

Referring back to step 306, if the temperatures are low enough to enable an inferred reference position, then the apparatus will be asked to randomly choose between either of the following possible dither sequences at step 310: (1) [inferred reference, dither]; or (2) [dither, inferred reference]. Conversely, if the temperatures are not low enough, then the apparatus will randomly choose between either of the following possible dither sequences at step 312: (1) [reference, dither]; or (2) [dither, reference].

Referring back to the question queried back at step 304, if the answer to the query at step 304 is negative, then the apparatus will invoke step 308. In step 308, the apparatus queries to determine whether in the previous dither pair, did we both: (1) end with a reference position; and (2) choose to stay with the reference position (i.e. was a new position not established and the reference position was last).

If the answer to the query at step 308 is negative, then the apparatus will randomly choose between either of the following dither sequences at step 312 as previously discussed.

If the answer is in the affirmative, then the apparatus will choose randomly either between (1) setting the dither sequence to [dither]; or (2) setting the dither sequence to [reference, dither] at step 314. In the case of (1), since a new reference position was not established in the previous dither pair and the reference position was last, processing time can advantageously be spared by simply re-using the measurements from the immediately prior measurement position.

Referring now to FIG. 3a (part 2 of 3), one exemplary embodiment of the process for executing the dither pair 316 is described in detail. At an abstract level, executing a dither pair according to the present embodiment is equivalent to reading the specific dither sequence previously determined and going to each specified position type in sequence. At each position we collect the beat data then move on to the next position specified in the sequence. At the conclusion of this iterative data collection enough data has been collected to make a decision on which position should be declared as our reference position.

At step 318, the next position type specified in the sequence is first queried to determine what position type it is. Depending on its position type, different algorithms or processing steps may be implemented in order to process and execute the respective dither pair. If the position type is an inferred reference position, then step 320 is invoked, while if it is a reference position or dithered position, steps 322 or 324 are invoked, respectively.

At step 320, the position type has been determined to be an inferred reference position by the apparatus. The reference position and the next target are set to a position that is a predetermined value (e.g. ⅓$^{rd}$) as far as the difference between the previous reference position and the previous dithered position beyond the previous dithered position. Mathematically, if our previous positions are designated $P_{Reference_{i-1}}$ and $P_{Dither_{i-1}}$, then the new reference position $P_{Reference_i}$ is computed as follows using Eqn. 2:

$$P_{Reference_i} = P_{Dither_{i-1}} + \frac{P_{Dither_{i-1}} - P_{Reference_{i-1}}}{2} \quad \text{(Eqn.2)}$$

If the position type has been determined to be a reference position, then the apparatus will set the target position to the current reference position at step 322.

If the position type has been determined to be a dithered position, then a dithered position is generated at step 324, requiring the generation, transformation and "baking" of a "unit dither" at step 326. The term "baking" refers in the present context to the process of modifying the value of the unit dither as a function of temperature. At step 324, the apparatus must first determine the axes that will be involved in the dither. These axes may include, but are not limited to, the Cartesian axes previously discussed (i.e. applanation, lateral, and distal axes). In one exemplary implementation, each dither can utilize movements in any combination of the actuator axes (i.e., the aforementioned applanation, lateral and distal axes) either serially or in parallel. The ability to move in more than one axis in parallel can potentially speed up the response for cases where the pulse pressure profiles are at steep angles with respect to the principle axes. However, for pulse pressure profiles that are largely parallel with the principle axes, single axis moves are often more beneficial. It is believed that most of these profiles are largely parallel, but not exactly parallel to, the principle axes. For purposes of robustness to alternate pulse pressure profiles, while at the same time acknowledging the nominal tendency for the profiles to be largely parallel to the exemplary actuator axes, a random mix of single and multiple axes dithers are performed in the illustrated embodiment, whose distribution is statistically controlled as a function of the current temperature.

Figure 3E:
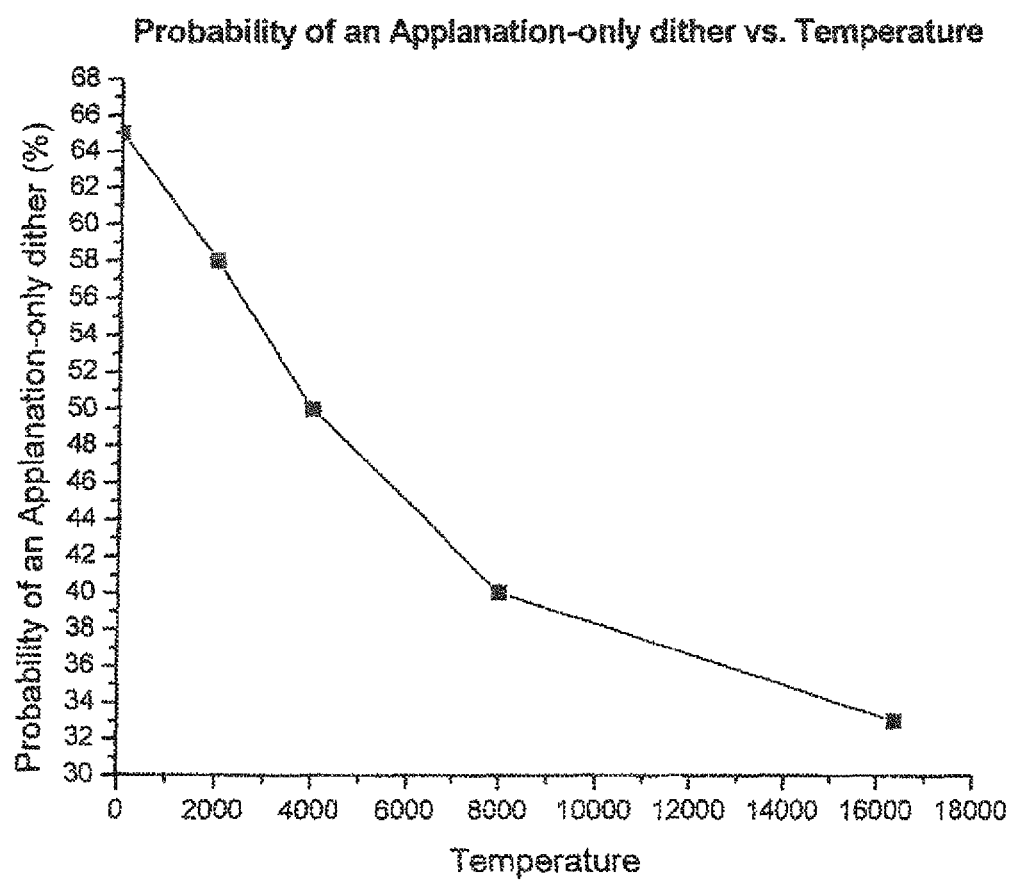
FIG. 3e is a graph illustrating the probability of an applanation-only dither as a function of temperature in accordance with one embodiment of the present invention.

At step 328, and in one exemplary embodiment, a 1-D interpolator is used to perform a piece-wise linear interpolation of the chart shown at FIG. 3e to determine the applanation axis only dither probability. This exemplary chart shown in FIG. 3e is constructed currently such that at high temperature values, the chart returns a value of 0.33, while at low temperature values it returns a value of 0.66. Thus in this example, applanation-only dithers are twice as probable at low temperature values, than at high temperature values. The remaining dithers will be equally divided between performing a lateral-only dither, or a combined applanation and lateral dither, etc. A substantially random number is generated in the closed interval [0, 1]. This random number is then tested, if the random number is less than the applanation-only probability, then only applanation will be involved in the next dither. If the random number is greater than or equal to the applanation-only probability; and is less than Eqn. 2, then only lateral movements will be involved in the next dither. If the random number is greater than or equal to Eqn. 3, then both applanation and lateral movements will be involved in the next dither.

$$1 - \left( \frac{1 - \text{applanation\_only\_probability}}{2} \right) \quad \text{(Eqn. 3)}$$

Referring now to FIG. 3b, the unit dither is generated, transformed and "baked". A unit dither is a unit less ordered N-Tuple of numbers, each of which is from the closed interval [−1, 1], with N being the number of axes of movement implemented in the exemplary actuator context. This N-Tuple of numbers is central to the process for generating randomized dithers for the simulated annealing algorithm described herein. For purposes of simplicity, it is assumed that the number of axes (N) in the example of the process of step 326 is equal to two (2), although more or less axes may be incorporated.

At step 330, the unit dither is generated. The apparatus first determines whether the unit dither generation is for a reference dither. If the result returns "true", then a unit dither of [0, 0] will be returned. If the result returns "false", then a randomly generated N-Tuple that resides in a unit cube is generated. Unit dither generation is first started by generating a random point within the unit cube. Although it is not desirable to end up with a unit sphere, using a spherical coordinate system to generate the random point will allow for a distribution of points such that most of the points will be concentrated at small radii. Random spherical generation will distribute points in such a way that the number of points at a given radius is nominally constant, thus this would imply lower densities at higher radii, as this constant number of points will be distributed over a larger circumference at the larger radii. To avoid this situation, random points are first generated in a Cartesian coordinate system, in effect guaranteeing a uniform distribution of points per unit volume.

Generating a randomly generated N-tuple is accomplished in one exemplary embodiment in the following manner. These steps are repeated for each of the N dimensions, here two (2), to generate the N-tuple.

First, a signed random number in the closed interval [-1, 1] is generated. Next, the concept of offset bias is introduced. Adaptive and axis-specific offset biases, each of which are constrained to values in the closed interval [-1, 1], are maintained to influence the distribution of the randomly generated dithers. For example, a dither offset bias value of zero in the illustrated embodiment indicates that there is no bias applied to the given dither generation for a given axis, while a value of 1.0 indicates that 100% of the time a positive going dither will be generated. Likewise a dither offset value bias of -1.0 indicates that 100% of the time a negative going dither will be generated. This concept is utilized to adaptively respond to evidence developed that indicates, for example, that the majority of successful dithers in the recent positioning history along the applanation axis were mostly negative. In this case, a negative dither offset bias will be generated to increase the likelihood of generating negative applanation dithers.

Using the current adaptively-determined offset bias for the given dimension i, $Bias_i$, $Bias_i$ is clipped to the closed interval of [-0.99, 0.99]. Bias is then calculated as being equal to 1 minus $Bias_i$. A random number R is generated in the closed interval [0, 1.0] and then a signed random number is calculated using Eqn. 4.

$$\text{SignedRandomNumber} = 2 \times R - \text{Bias} \quad \text{(Eqn. 4)}$$

If SignedRandomNumber is greater than zero, then Eqn. 5 is used; if it is less than zero, Eqn. 6 is used. The $i^{th}$ component of the N-Tuple is set to the newly calculated SignedRandomNumber.

$$\text{SignedRandomNumber} = \text{SignedRandomNumber} \times 1.0 \div (2.0 - \text{Bias}) \quad \text{(Eqn. 5)}$$

$$\text{SignedRandomNumber} = \text{SignedRandomNumber} \times 1.0 \div \text{Bias} \quad \text{(Eqn. 6)}$$

The unit dither specification is then tested for compliance. The radius of the unit dither is computed, and exemplary logic determines whether the radius of the unit dither is less than or equal to one, to ensure that the point falls inside of the unit sphere. If the unit dither falls within the unit sphere, then the logic determines if the radius is greater than or equal to 0.5. This test is utilized to avoid the generation of small dithers relative to the maximum possible given the current temperature.

If greater than or equal to 0.5, the square of the radius is calculated, while either serially or in parallel a random number is generated in the closed interval [0, 1]. If the random number generated is less than or equal to the square of the radius, then the unit dither passes the criteria established and the result is returned. If any of these tests fail, unit dither generation is repeated.

In step 332, the unit dither is transformed to a number with physical units to guide the actuator movement. The transformation process converts this unit less N-tuple into a similar N-tuple, but with physical units. Note, however, that the units may be different depending on the axis that it controls. For instance applanation units in the transformed unit dither may be in mm-Hg, although this is by no means a requirement, thus allowing for a tissue compliance-related response farther downstream in the apparatus code. Similarly units for lateral position may use finer units than that used for distal position, to account for differences in the potential range between these two axes. It is in this step that nominal differences in travel, i.e. aspect ratio, between the various axes are taken into account.

First, for each axis in the N-tuple of the unit dither specification, the axis-specific component in the N-tuple will be transformed. The maximum specified dither travel for the given axis $Dither_{max}$, will then be obtained. In one embodiment, this quantity will be fixed at the compile time of the software implementing the algorithm, and will represent the nominal maximum dither to be generated for the given axis, though run-time adaptations can cause the generations of yet larger dithers when determined to be appropriate. The $i^{th}$ component of the N-tuple is then transformed into physical units using Eqn. 7.

$$Dither_i = Dither_{max_i} \times \text{Unit\_dither}_i \quad \text{(Eqn. 7)}$$

The adaptively determined aspect ratio is then applied. "Aspect ratio" as used in the context of the present embodiment specifically refers to the aspect ratio between the applanation and lateral and/or distal axes, etc., however for simplicity it will be only discussed as the ratio between applanation and lateral. In this particular embodiment, this more specifically refers to the ratio of the maximum applanation dither to the maximum lateral dither (or derivative quantities relating thereto). At compile-time, a fixed nominal aspect ratio is defined such that a given unit dither specification of [1, 1], the resulting dither will have an applanation displacement versus a lateral displacement that are related by this nominal aspect ratio. In other words, the nominal aspect ratio defined at compile-time allows the code to abstract these nominal differences away, and therefore can largely concentrate instead on the run-time tweaks to this basic relationship.

An aspect ratio "tweak" in the present context is an adaptively determined quantity that is signed and has values in the closed interval [-1, 1]. A value of "0" implies that no adaptation is necessary in the dither aspect ratio. A positive value indicates that over-and-above the nominal aspect ratio, applanation should be further emphasized, and a negative value indicates that lateral should be further emphasized. In actual implementation when, e.g., an applanation emphasis is called for, (i.e. an aspect ratio "tweak">0), "half" of this emphasis is placed upon the applanation axis, and "half" of this is used to de-emphasize the lateral axis. In this way, disruptions resulting from too large a degree the nominal vector length of the dither being generated are advantageously avoided. If for instance, the applanation axis has an aspect ratio tweak value that is positive, the applanation dither is further emphasized. Note also that the use of "half" of the aspect ratio tweak on the applanation axis, and the other half on the lateral axis is meant purely in a geometric sense; hence the use of the square root in Eqn. 8. The invention is in no way limited to such "half" or other schemes, however. Conversely, if the applanation axis has an aspect ratio tweak value that is negative, Eqn. 9 is used which effectively de-emphasizes further the applanation dither.

$$Dither_i = Dither_i \times \sqrt{1.0 + |aspect\_ratio\_tweak|} \quad \text{(Eqn. 8)}$$

$$Dither_i = Dither_i \times \frac{1}{\sqrt{1.0 + |aspect\_ratio\_tweak|}} \quad \text{(Eqn. 9)}$$

An adaptively determined aspect ratio adjustment for pulse pressure curve asymmetry is then applied. This is done in order to account for the typical pulse pressure curve asymmetries found irrespective of whether the device is currently operating above or below the patient's mean pressure. It has been found by the inventors hereof that pulse pressure slopes above the patient's mean pressure roll-off at a much steeper rate than the pulse pressure rise below the patient's mean pressure. In other words, when above the patient's mean pressure, there is a need to de-emphasize the applanation axis dither, while this dither should be emphasized when below the patient's mean pressure.

The adaptively determined dither offset values can be utilized to give an indication whether or not the apparatus is largely applanating or de-applanating. If the apparatus is largely applanating, then it can be deduced that pulse pressure readings may be below the patient's mean pressure. Conversely, if the apparatus is largely de-applanating, then it is likely that the readings are above the patient's mean pressure. Through studies conducted by the Assignee hereof, it has been determined that this ratio is roughly 260%; that is, the pulse pressure slopes are approximately 2.6 times steeper above the patient's mean than below it. Therefore, given AboveVsBelowMeanPPRatio=2.60, the application ratio tweak is calculated using Eqn. 10 where the AppOffset value is greater than or equal to zero, otherwise Eqn. 11 is used.

$$AppTweak = \frac{1}{1 + \left(\sqrt{AboveVsBelowMeanPPRatio} - 1\right) \times |AppOffset|} \quad \text{(Eqn. 10)}$$

$$AppTweak = 1 + \left(\sqrt{AboveVsBelowMeanPPRatio} - 1\right) \times |AppOffset| \quad \text{(Eqn. 11)}$$

Thus, the dither value at each position i is calculated using the value obtained by either Eqn. 10 or Eqn. 11 using Eqn. 12.

$$Dither_i = Dither_i \times AppTweak \quad \text{(Eqn. 12)}$$

Similarly, if it is desired to de-emphasize (using Eqn. 13) or emphasize (Eqn. 14) other axes, such as the lateral axis, this can be calculated as well using similar aspect ratio tweaks.

$$Dither_i = Dither_i \times \frac{1}{\sqrt{1.0 + |aspect\_ratio\_tweak|}} \quad \text{(Eqn. 13)}$$

$$Dither_i = Dither_i \times \sqrt{1.0 + |aspect\_ratio\_tweak|} \quad \text{(Eqn. 14)}$$

Following the transformation process of the unit dither, the unit dither is now "baked" at step 334. The term "baking" refers in the present context to the process of modifying the value of the unit dither as a function of temperature. It is generally expected that a response at high temperatures (i.e. correlating to a lower confidence that the transducer is located properly) the system should be displaced more, while at lower temperatures the system is expected to be displaced less.

In one embodiment, the transformed unit dither is baked by first obtaining the current "taxed" temperature for each axis. "Taxing", as the name implies, is the core system temperature with an added "tax"; here a generic and arbitrary quantity that can be used for multiple purposes. A tax can be applied to the temperature for various reasons, but in general it is used to penalize the system, or perhaps put it in an increased state of perturbation or awareness. In this embodiment, the temperature is taxed only when the current mean pressure is particularly high or low (as determined against, e.g., predetermined or variant criteria), corresponding to the likelihood that the value is not correct.

It should also be noted that in the current embodiment, a temperature can be used either taxed or not taxed and thus at any one time both versions can be made available in the system. In an alternate embodiment, each axis will have a temperature equivalent to the system-wide core temperature.

Figure 3F:
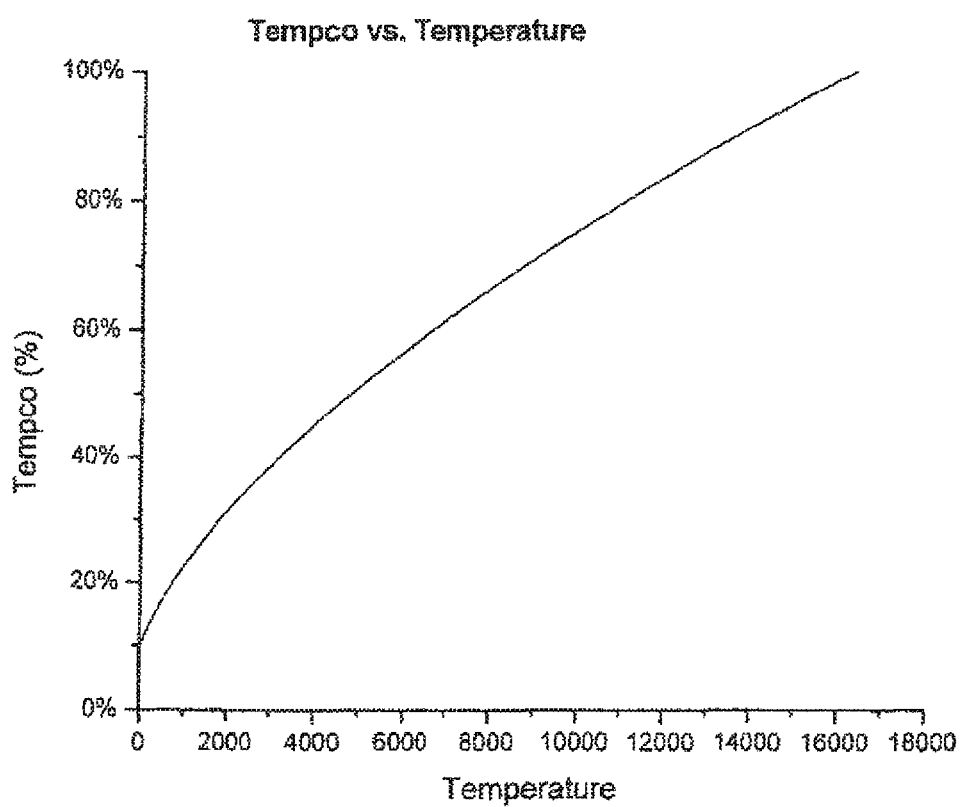
FIG. 3f is a graph illustrating the temperature coefficient as a function of temperature in accordance with one embodiment of the present invention.
Figure 3G:
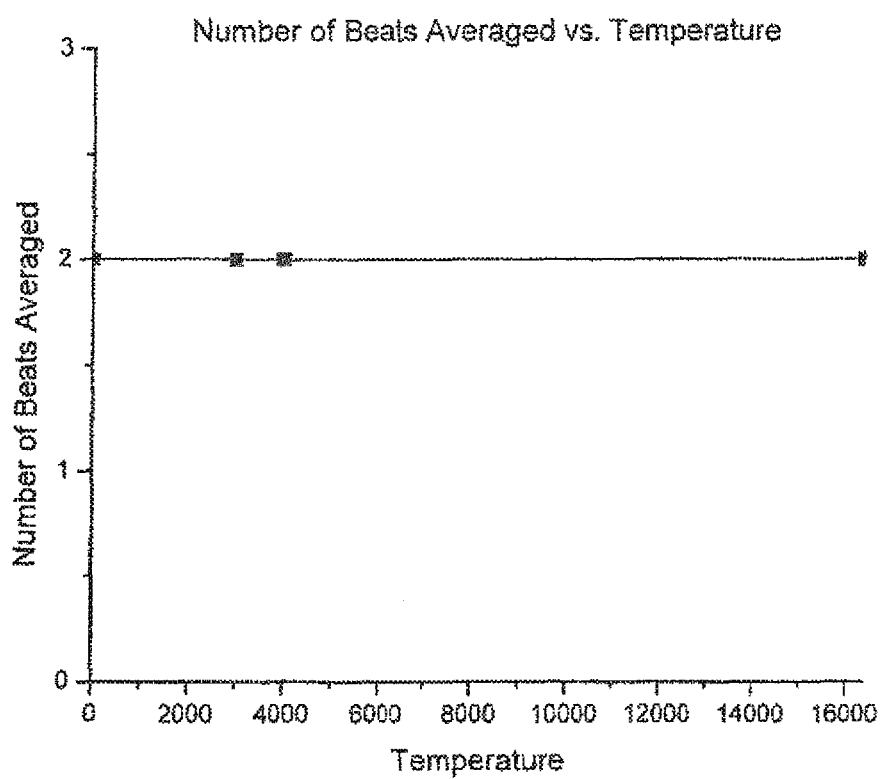
FIG. 3g is a graph illustrating temperature as a function of number of beats to collect in accordance with one embodiment of the present invention.

Referring now to FIG. 3f, the temperature coefficient is determined using a 1-D interpolator to perform a piece-wise linear interpolation of the chart depicted in FIG. 3f. The baked dither is then calculated using Eqn. 15.

$$Dither_i = tempco \times Dither_i \quad \text{(Eqn. 15)}$$

Referring again back to FIG. 3a (part 3 of 3), in step 336 the apparatus advances to the target position, regardless of whether it was an inferred reference position, reference position or a dithered position. If the target position is not reached within a predetermined amount of time (e.g. 1.5 seconds), then the system times out on this dither and notifies the system while aborting the simulated annealing process.

If the target position is reached in time, the beat data is collected at step 338. The process for collecting beat data is described in detail below with regards to FIG. 3c and its accompanying disclosure.

After collection of the beat data, the system determines whether the last position was the last position type in the sequence at step 346. If it is not, the whole process repeats starting at step 318. If it is the last position in the sequence, the algorithm advances to hemodynamic parameter processing.

(3) Hemodynamic Parameter Processing

Referring now to FIG. 3c, the collection of beat data 338 is described in detail. At step 340, the number of beats to collect is determined. In one embodiment, the number of beats to collect is fixed at a predetermined number (e.g. two (2)). Alternatively, in a second embodiment, the number of beats is collected as a function of one or more parameters (e.g., temperature). In this example, a piece-wise linear interpolation of the chart of FIG. 3f (Temperature vs. Beats to Collect) is used to determine the baseline number of beats to be collected.

In a third embodiment that can be used either alone or in conjunction with either of the two previous embodiments, (computer or algorithmic) logic determines whether the core temperature value is below a certain threshold (e.g. 2000). If so, then a statistical algorithm is employed which first generates a random number in the closed interval [0, 1] and tests this random number to see whether it is either higher or lower than the midpoint of the interval (i.e. 0.5). If it is less than the midpoint, a pre-specified number of beats are added (e.g. one (1)), while if the random number is greater than the midpoint, the number of beats to detect is left at the existing value.

The reason for the foregoing approach utilized in this third embodiment is that at low temperatures, there are conflicts between two opposing needs. As the vast majority of dithers will occur at lower temperatures, the decisions made at these low temperatures would benefit by as little noise as is practicable. On the other hand, it is undesirable to sacrifice a rapid response to large changes, and to a large degree the noise is taken out in the long run as the results of consecutive dithers that are cumulative in nature.

Furthermore it has been observed that at low temperatures, the resultant dithers of these decisions are small in nature and that they therefore do not by themselves have a large impact on these decisions. So in response, an approach is taken that statistically adds in the equivalent of an additional "half a beat" on average at these low temperatures.

Therefore, at these lower temperatures, half of the time the number of beats are taken as normally would be determined given the current temperature, etc., and the other half of the time, one additional beat is taken under this third embodiment.

At step 342, beat detection is delayed for a predetermined amount of time. This beat delay detection is utilized to account for delays such as (1) group delays in batch processing; or (2) for settling time after a dither. In one embodiment, these delays are set to 250 ms and 125 ms respectively, accounting for a total delay of 375 ms, although it will be recognized that other values may be used.

At step 344, the apparatus waits for either a beat timeout or a detected beat. A beat timeout in the present context comprises the absence of a detected beat during any designated epoch of time, such as e.g., five (5) seconds. While primarily envisioned as only utilizing a pre-established epoch of time, certain embodiments of the present invention may extend, contract or adapt this timeout as conditions change within the system. For example, after a detected motion event, the wait period may be reset, re-establishing the full designated epoch of time. Alternatively, after a detected motion event, the wait period may be extended for a specified period of time.

If on the other hand a beat is detected, the exemplary apparatus executes logic which determines whether the detected beat occurred within a prescribed period (e.g., one second) of a previously detected motion event. If it has, then the beat is ignored. If not, the beat is stored for later processing. For example, in one embodiment, the detected beat is added to previously detected beats to keep a running average calculation of mean pulse pressure values over the duration of the beat collection cycle.

Figure 4:
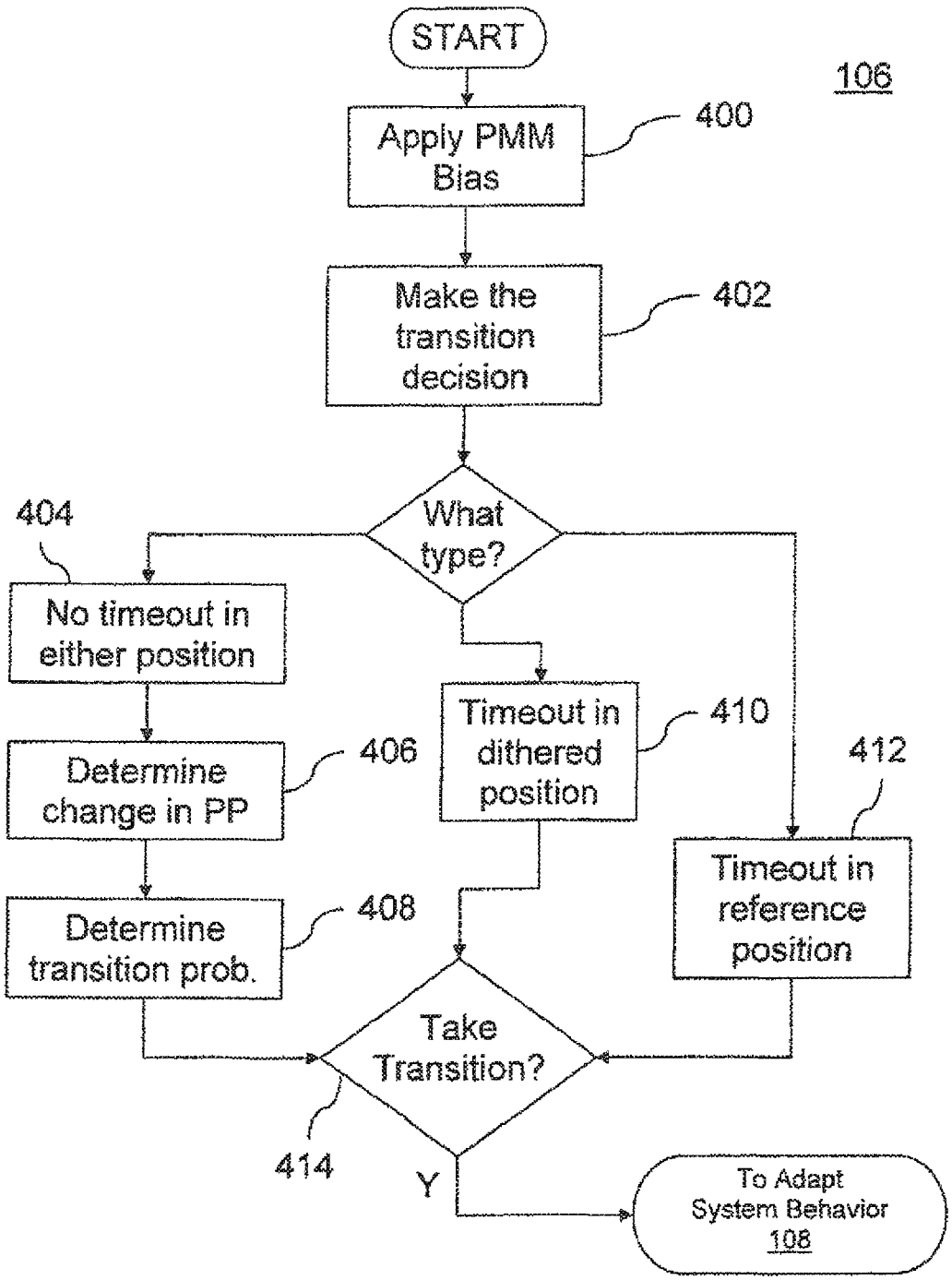
FIG. 4 is a flow diagram illustrating the operation of one exemplary embodiment of the third process (e.g. hemodynamic parameter processing) according to the invention.

Referring now to FIG. 4, the hemodynamic parameter processing step 106 of FIG. 1 is described in detail.

At step 400, patient monitoring mode (PMM) bias is applied to the measured pulse pressure difference. PMM bias is a correction that is applied to the measured pulse (pulsatile) pressure difference in order to correct what has been observed as flat pulse pressure curves. It has been observed through experiment by the Assignee hereof that when the pulse pressure versus mean pressure curves becomes flattened, the peak in this curve occurs at a place that is actually higher than the patient's mean pressure. The flatter the curve becomes, the larger this offset appears to be. As the peak in this pulse pressure curve is used as a basis to determine the patient's mean pressure, a corrective bias is applied in order to shift the peak towards lower pressure to correct for this phenomenon.

This shift is such that it will typically be larger for flatter curves, and smaller for sharper curves. In one embodiment, this factor has been set to 35% (0.35). However, in order to avoid issues of these bias values lowering pressures too far, various measures are taken to curtail its effect. In one exemplary embodiment, the PMM bias in step 400 is applied as follows using Eqn. 16 and Eqn. 17:

$$\Delta PP = PP_{dither} - PP_{ref} \quad \text{(Eqn. 16)}$$

$$\Delta Mean = Mean_{dither} - Mean_{ref} \quad \text{(Eqn. 17)}$$

Figure 4A:
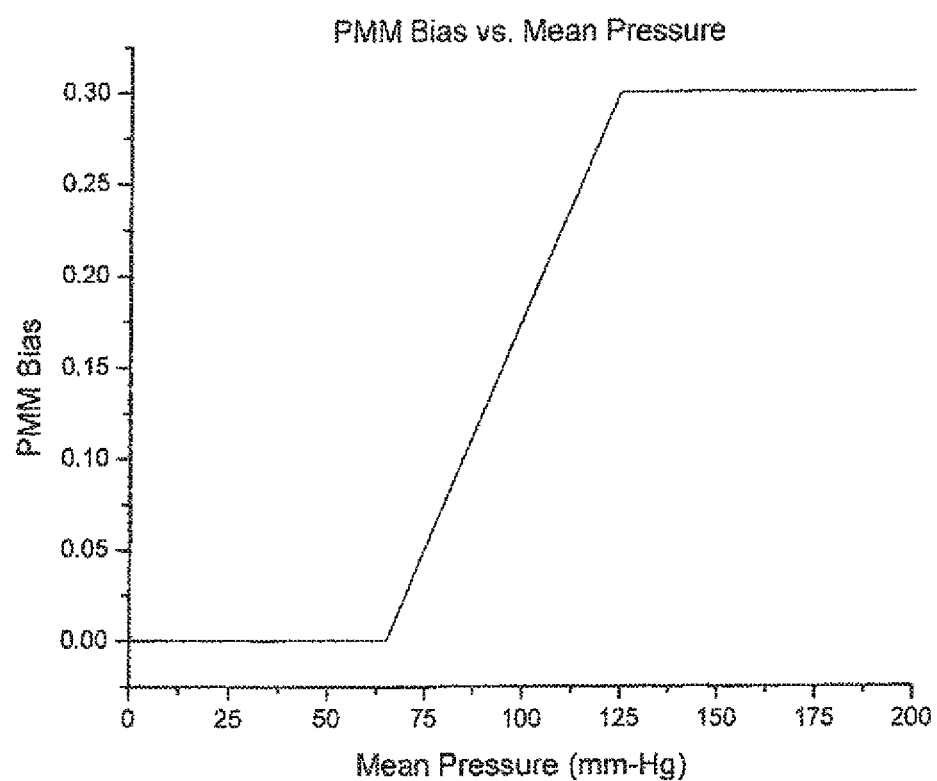
FIG. 4a is a graph illustrating PMM bias as a function of mean pressure in accordance with one embodiment of the present invention.
Figure 4B:
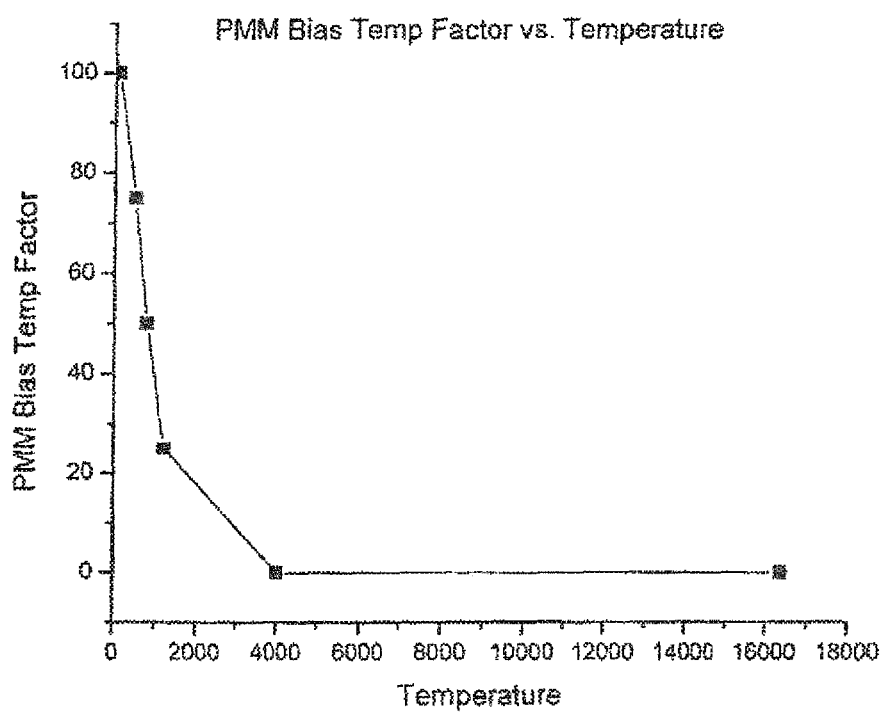
FIG. 4b is a graph illustrating PMM bias temperature factor as a function of temperature in accordance with one embodiment of the present invention.

After performing these two calculations, the PMM bias is determined by performing a piece-wise linear interpolation of the reference mean as a function of PMM bias (chart shown in FIG. 4a) to determine the nominal PMM bias to use. This linear interpolation can be performed by using an interpolator (e.g. a 1-D interpolator). After obtaining the current taxed (or in some embodiments, untaxed) temperature, a piece-wise linear interpolation of the temperature as a function of PMM bias temperature factor is determined using a chart such as that shown in FIG. 4b. The addition of the pulse pressure bias is then performed thusly using Eqn. 18, Eqn. 19 and Eqn. 20:

$$PMMBias_{composite} = PMMBias_{nominal} \times k_{temp} \quad \text{(Eqn. 18)}$$

$$PP_{bias} = -\Delta Mean \times PMMBias_{composite} \quad \text{(Eqn. 19)}$$

Note that the term on the right side of Eqn. 19 is negative to reflect that the higher the mean pressure difference is, the more the pulse pressure difference should be de-emphasized.

Clip $PP_{bias}$ to the closed interval $[-1.2, 1.2]$ mm-Hg; and (Eqn. 20)

Calculate $\Delta PP = \Delta PP + PP_{bias}$ (Eqn. 20)

Next, the algorithm must make the transition decision at step 402. This transition decision is based on a combination of where the timeout occurred, and in which position (dithered and/or reference). If no timeout occurred in either position (i.e. dithered and reference), which is the most typical case, then pulse pressure change is determined using Eqn. 21 at step 406.

$$PP_{change} = PP_{dither} - PP_{reference} \quad \text{(Eqn. 21)}$$

At step 408, the transition probability is determined. In simulated annealing, transition probabilities are based upon both the change in energy, (the negative of the change in pulse pressure in one embodiment), and the current temperature. While the transition probability is normally set to 100% if there is a decrease in energy, (simulated annealing attempts to lower the total energy of a system; this is equivalent to an increase in pulse pressure in the exemplary implementation for a hemodynamic system), there are a variety of responses for the cases of no change in energy, or for an increase in energy state. This feature in large part gives simulated annealing its inherent ability to be able to move away from locally optimal areas and find what would be the global optima. In essence, it is the ability to occasionally, in a metered way and under strict control, advance a move towards a higher energy (lower pulse pressure) state, that provides many of the benefits of the simulated annealing control process.

Figure 4C:
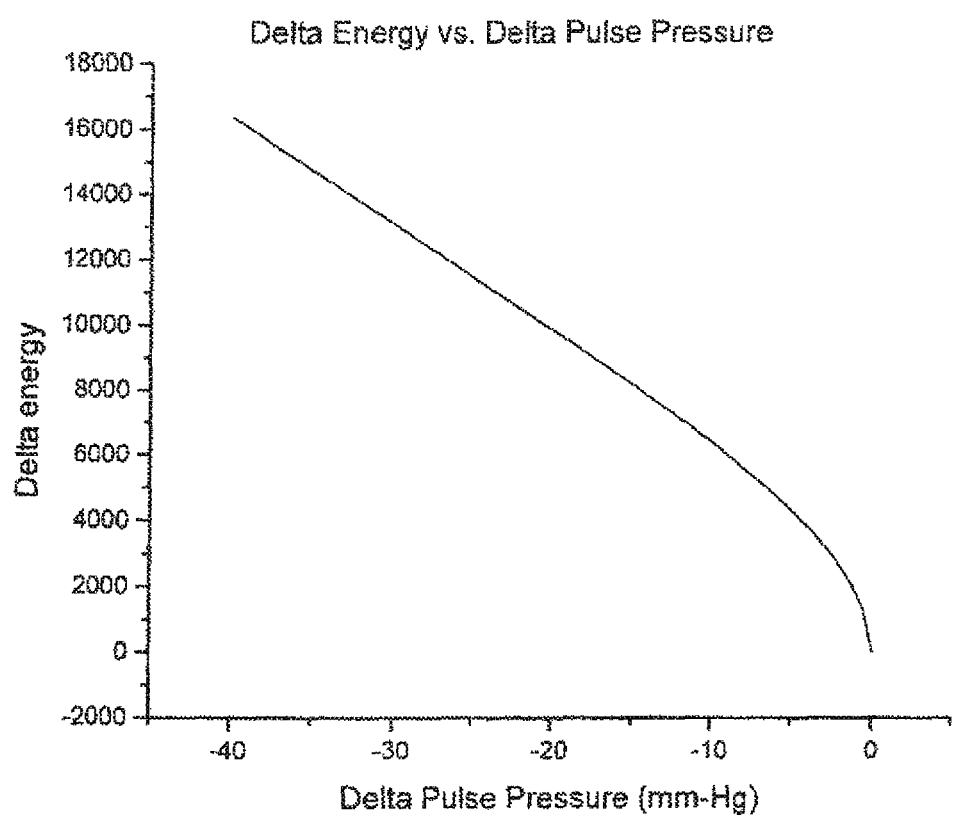
FIG. 4c is a graph illustrating delta energy as a function of delta pulse pressure in accordance with the principles of the present invention.

In step 408, the change in energy is determined using a piece-wise linear interpolation of the ΔEnergy as a function of ΔPressure (see chart of FIG. 4c). Note that the chart and linear interpolation are only used for changes of pulse pressure that are negative. If the ΔEnergy is negative, the transition probability is set to 1.0. If the ΔEnergy is equal to zero, then the transition probability is set to 0.5. If the ΔEnergy is positive (i.e., the dithered position resulted in a smaller pulse pressure)

and the current temperature is greater than a prescribed value (e.g., 500), then the transition probability is set to zero. However, if the ΔEnergy is positive and the current temperature is less than 500, then a 2-D interpolator is used to perform a bi-linear interpolation of the transition probability as a function of temperature, and the delta energy chart of FIG. 4c is utilized to determine the transition probability.

At step 410, if the timeout was only in the dithered position, or was in both the reference and dithered positions, then the transition probability is set to zero. Conversely, at step 412, if the timeout only occurs in the reference position, then the transition possibility is set to 1.0.

At step 414, a decision is made about whether to take the transition or not. In one embodiment, the apparatus will generate a random number in the closed interval [0, 11]. If the random number is less than the transition probability then the system will take the transition towards the dithered position, otherwise it will start with the current reference position.

(4) Adaptive Behavior

Figure 5:
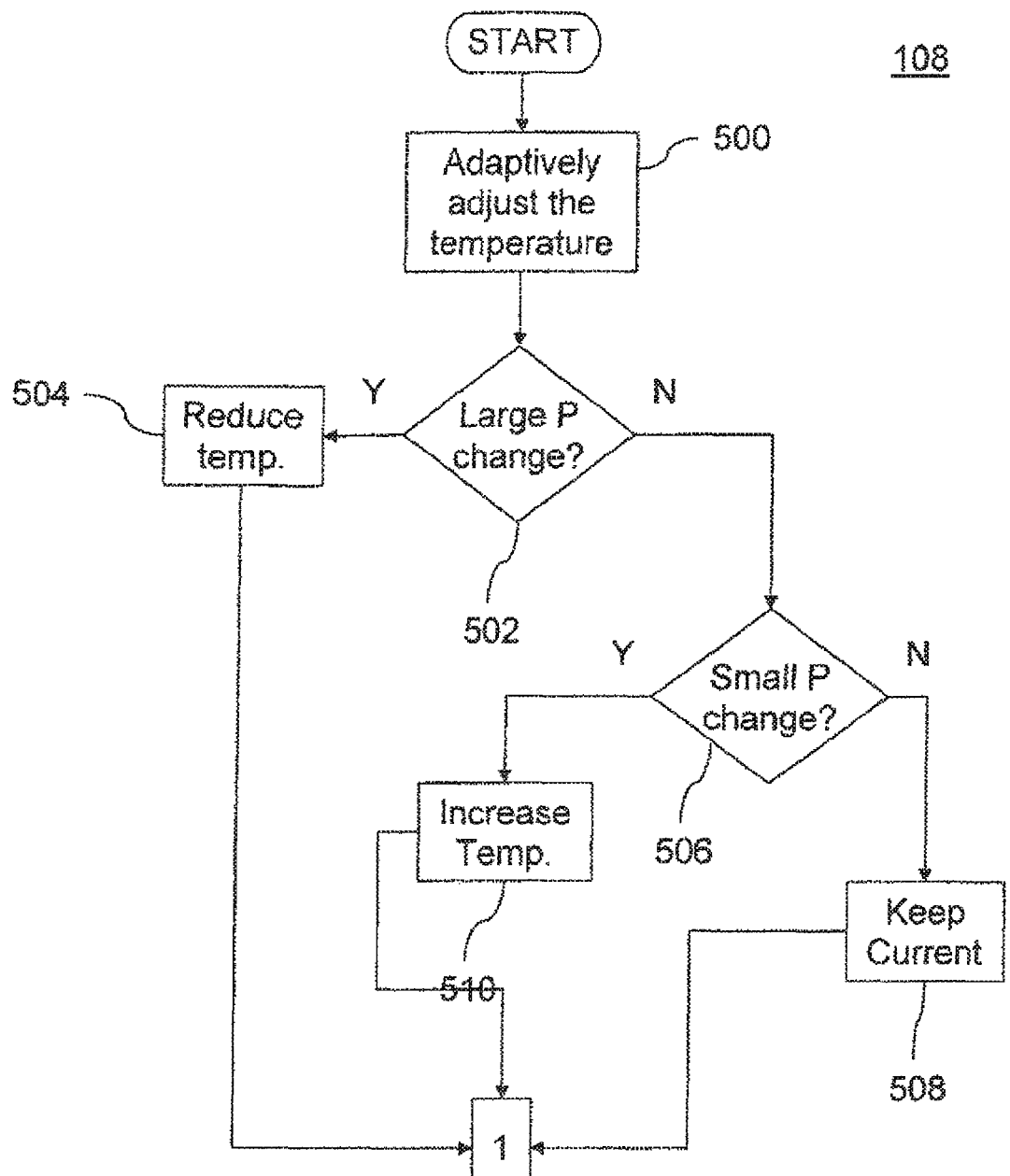
FIG. 5 is a flow diagram illustrating the operation of one exemplary embodiment of the fourth process (e.g. adapting behavior of system) of FIG. 1.
Figure 5:
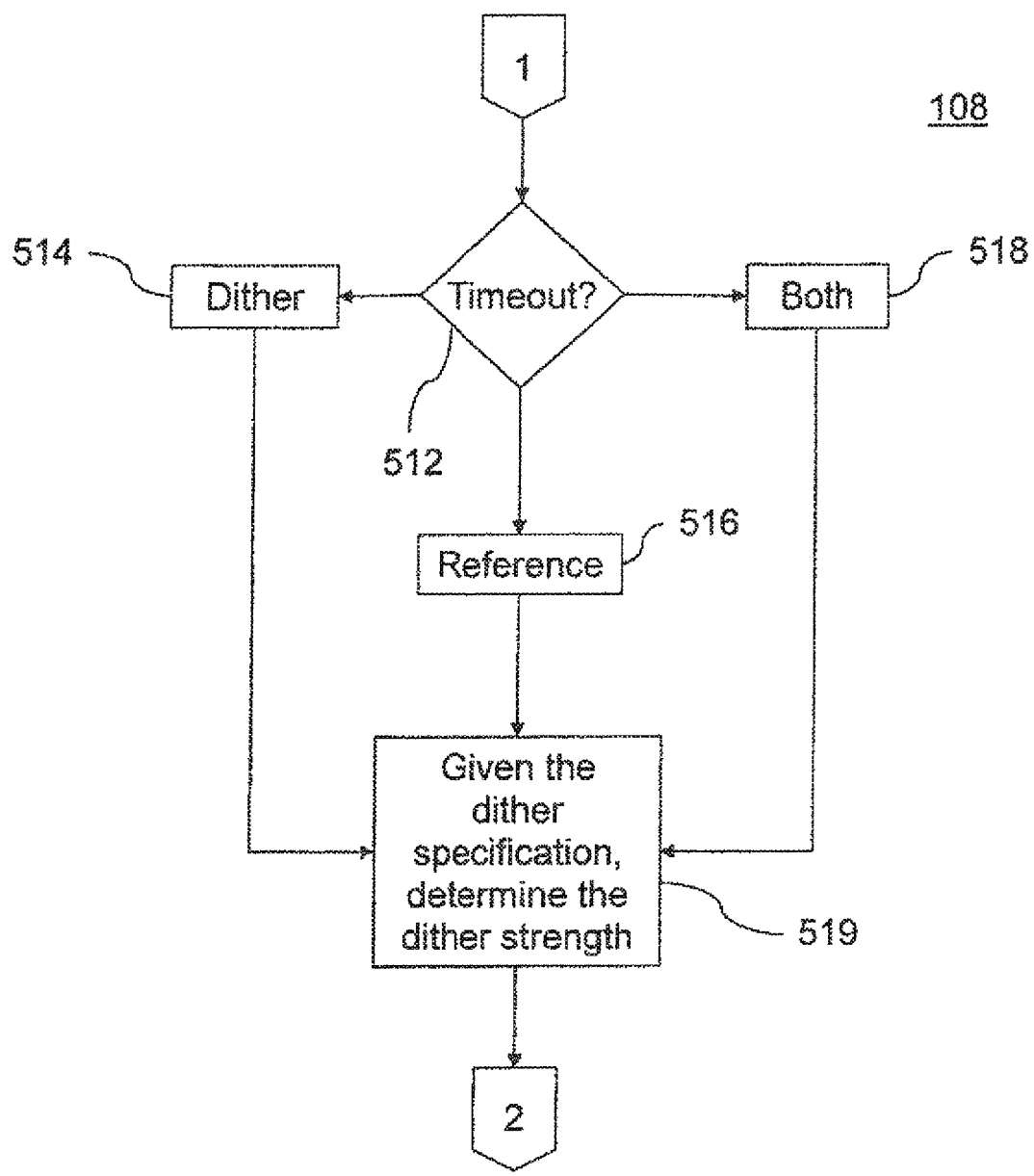
Figure 5:
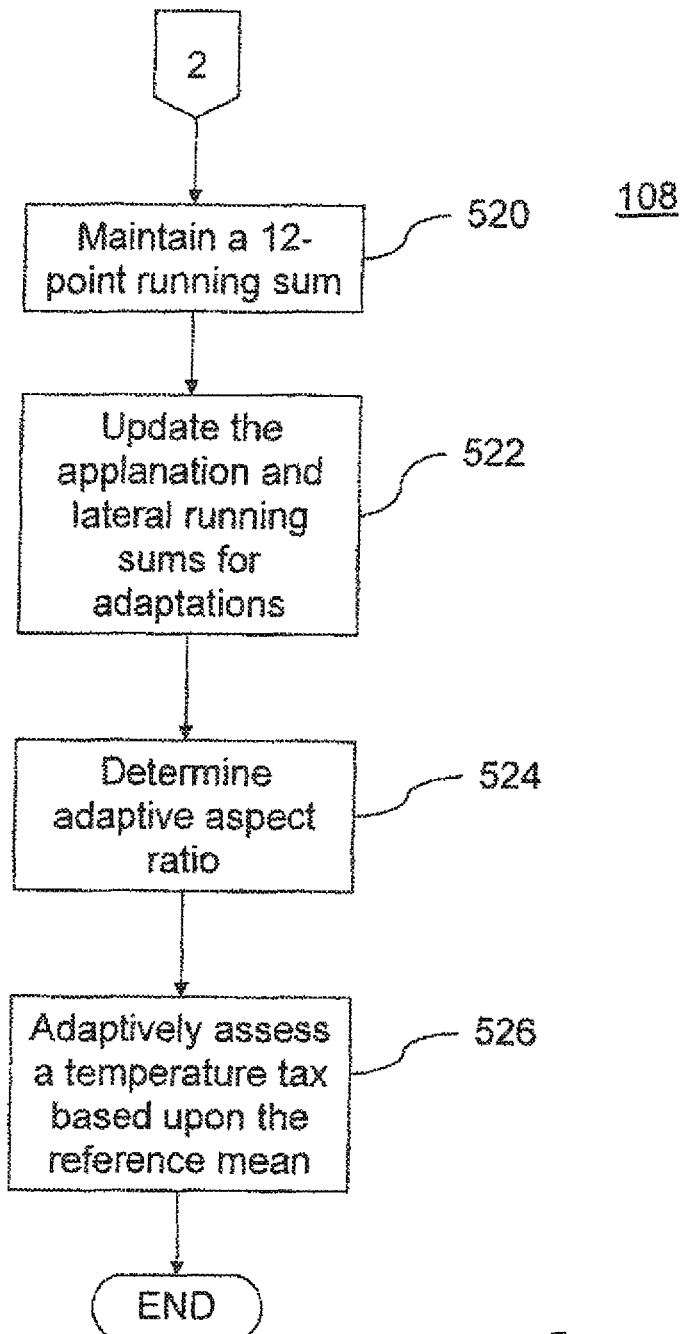

Referring now to FIG. 5, an exemplary embodiment of the adaptive adjustment algorithm of the invention is described.

Per step 500 the temperature is adaptively adjusted. Note that the exemplary adjustments described herein are subject to limits beyond which the adjustment will not take effect. For temperature increases, the limit imposes a maximum, and for temperature decreases, the limit imposes a minimum. In adjusting the temperature, the timeout pattern is also analyzed. In the nominal case (i.e. where there is no timeout), signs of excessive modulation of the pulse pressure are identified by determining whether or not there was a large pressure change (step 502). In one exemplary embodiment, this determination is accomplished in a two-step process. First, logic determines whether the large pulse pressure is greater than a prescribed value (e.g., fifteen (15) mm-Hg). If not, the logic returns "false"; otherwise logic then queries whether the smaller pulse pressure is less than or equal to a given percentage (e.g., 60%) of the larger pulse pressure. If it is, then the logic returns "true", otherwise it returns "false". While the threshold limits of fifteen mm-Hg and 60% of the larger pulse pressures have been chosen for this example, it is understood that these numbers may vary considerably from application to application, the aforementioned numbers merely being exemplary.

If the pressure change was too large in magnitude (i.e., the logic has returned true), then the temperature is reduced (e.g. by a prescribed increment such as 2 "clicks") at step 504. If there was not a large instant pressure change, logic then determines whether or not there was a large mean pressure change to determine whether the mean pressure is being excessively modulated. In one embodiment, if the mean pressure change increases by more than 35 mm-Hg, then the logic will return "true" and the temperature will be decreased by a set amount (e.g. two (2) clicks). If not, then logic determines if there was too small of a pulse pressure or mean pressure change at step 506. This is to ensure that at least a minimal amount of both pulse pressure and mean pressure modulation is applied to the system.

In one variant, if the absolute pulse pressure change is less than 1 mm-Hg, then the logic will return "true", otherwise it will determine if the absolute mean pressure change is less than 1.5 mm-Hg, and then return "true" if the answer is yes, otherwise it will return "false". If logic determines the change was too small, then the temperature is increased at step 510 (e.g. by 1.3 clicks), otherwise the temperature is kept current (step 508).

Note however that the aforementioned process (i.e. steps 502-510) are applicable when there has been no timeout observed. At step 512, logic determines whether there was a dither beat timeout, a reference beat timeout, or both. At step 514, the occurrence of a dither beat timeout event normally suggests that the system may have been dithered too much so as to lose the beat at the dithered position. This suggests a temperature that is too high if the assumption that has been made is correct. However, if the reference beat is not strong either, then there is a risk of losing the reference beat as well by dithering too much, and inducing too much large signal behavior.

Therefore, before assuming that the initial assumption was a valid one, logic is used in the exemplary algorithm to determine whether the reference beat pulse pressure is greater than a minimum amount (e.g. 10 mm-Hg), which is to ensure that reducing temperature does not raise the possibility that the reference beat may be lost by any large temperature changes to the system. If the reference beat pulse pressure is greater than the minimum amount, then the temperature is decreased. In one exemplary embodiment, the temperature is reduced by three (3) clicks, otherwise no change is made.

At step 516, if there was only a reference beat timeout, then the temperature is increased. In one embodiment, this temperature increase is 1.5 clicks, although other values may be used.

At step 518, if there is both a reference and a dither beat timeout, then the temperature is increased. In one embodiment, this temperature increase is by 2.5 clicks. Note that in the illustrated embodiment, the temperature increase for this second condition (both timeouts) is larger than for the reference-only timeout, since greater correction magnitude is ostensibly required.

At step 519, respective dither strengths are determined given the dither specification. Dither strength is a characterization of the degree to which a particular dither was deemed to be either strongly lateral or strongly applanation, etc., or alternatively the degree to which it was strongly neither. Recall that in general, random dithers have been taken along all of the participating axes, however in order to tune various adaptive parameters it is often important to collect data on the effectiveness of the dithers taken primarily along one of the principle axes. In one embodiment, a strong predominantly signal-axis dither is taken to be one whereby its normalized dither, equivalent to its mapping in the unit sphere, is within 30 degrees of a principle axis. In one exemplary embodiment, the dither strength is determined as follows:

Step One: Normalize the applanation and lateral dither amounts using Eqn. 22;

$$k_{app} = \frac{Dither_{app}}{Dither_{max_{app}}};$$ (Eqn. 22)

and $$k_{lat} = \frac{Dither_{lat}}{Dither_{max_{lat}}}$$

Step Two: If $k_{app}=0$ and $k_{lat}=0$, return neutral, otherwise;
Step Three: Test the lateral dither amount using Eqn. 23

$$k_{lat}^2 \leq 0.25 \times (k_{app}^2 + k_{lat}^2)$$ (Eqn. 23)

Step Four: If yes to step three, then test $Dither_{app}>0$. If yes, return App_Is_Strongly_Positive, otherwise return App_Is_Strongly_Negative;

Step Five: If no to step three, then test the applanation dither amount using Eqn. 24

$$k_{app}^2 \leq 0.25 \times (k_{app}^2 + k_{lat}^2).$$ (Eqn. 24)

Step Six: If yes to step five, then test Dither$_{lat}$>0. If yes, return Lat_Is_Strongly_Positive, otherwise return Lat_Is_Strongly_Negative; If no to step five, then return neutral.

At step 520, a 12-point running sum for both applanation and lateral movements is recorded.

It will be recognized that while the foregoing process is described with respect to lateral and/or applanation axes or dimensions, others may be used, either in place of the foregoing, or in conjunction therewith (or even in different permutations), as will be readily implemented by those of ordinary skill given the present disclosure.

At step 522, the applanation and running sums for the adaptations are updated. In a first embodiment, these sums are updated as follows.

If App_Is_Strongly_Positive is returned, then logic determines whether the transition to the dither was taken. If yes, the applanation running sum is fed a value of two (2), otherwise it is fed a value of negative one (−1).

If App_Is_Strongly_Negative is returned, then logic determines whether the transition to the dither was taken. If yes, the applanation running sum is fed a value of negative two (−2), otherwise it is fed a value of one (1).

If Lat_Is_Strongly_Positive is returned, then logic determines whether the transition to the dither was taken. If yes, the lateral running sum is fed a value of two (2), otherwise it is fed a value of negative one (−1).

If Lat_Is_Strongly_Negative is returned, then logic determines whether the transition to the dither was taken. If yes, the lateral running sum is fed a value of negative two (−2), otherwise it is fed a value of one (1).

If nothing is returned, nothing is added to the running sums.

At step 524, the adaptive aspect ratio is determined. First, however, a similarity score that measures how similar the applanation and lateral values are, a dissimilarity score that determines how dissimilar the applanation and lateral values are and the categorization strength score that measures the extent to which the similarity and the dissimilarity scores can be trusted needs to be determined. The equations for these calculations are shown below as Eqn.'s (25) through (28).

$$Score_{app} = \frac{RunningSum_{app}}{24}; \text{ and } Score_{lat} = \frac{RunningSum_{lat}}{24} \quad \text{(Eqn. 25)}$$

$$Score_{similarity} = \begin{cases} 1.0, & |Score_{app}| = 0 \& Score_{lat} = 0 \\ \frac{Min(|Score_{app}|, |Score_{lat}|)}{Max(|Score_{app}|, |Score_{lat}|)} & \text{otherwise} \end{cases} \quad \text{(Eqn. 26)}$$

$$Score_{dissimilarity} = \begin{cases} 0.0, & |Score_{app}| = 0 \& Score_{lat} = 0 \\ \frac{Max(|Score_{app}|, |Score_{lat}|) - Min(|Score_{app}|, |Score_{lat}|)}{|Score_{app}| + |Score_{lat}|} \end{cases} \quad \text{(Eqn. 27)}$$

$$Score_{categorization\_strength} = \frac{Max(|Score_{similarity}|, |Score_{dissimilarity}|) - Min(|Score_{similarity}|, |Score_{dissimilarity}|)}{|Score_{similarity}| + |Score_{dissimilarity}|} \quad \text{(Eqn. 28)}$$

Next, if the variable $Score_{categorization\_strength} \geq 0.35$ then logic determines whether or not $Score_{dissimilarity} > Score_{similarity}$. If not, then the scores are said to be too unequivocal or indefinite, and hence cannot be acted upon. In this case, the aspect ratio will be slowly decayed towards zero, which is generally the safest place to be whenever in doubt. In one embodiment, the aspect ratio is thus calculated using Eqn. 29:

$$k_{AspectRaito} = 0.85 \times k_{AspectRatio} \quad \text{(Eqn. 29)}$$

If however, the parameter $Score_{categorization\_strength} \geq 0.35$, but $Score_{dissimilarity} < Score_{similarity}$, then this is an indication that the scores are probably similar. The aspect ratio should thus be affected by the confidence of a similarity, however to be more careful, the aspect ratio is approached geometrically rather than by making a sudden change to a new value. Recall that our target aspect ratio for a similarity is simply towards zero. The aspect ratio is thus in one embodiment calculated as:

$$k_{AspectRatio} = 0.4 \times k_{AspectRation} \quad \text{(Eqn. 30)}$$

If $Score_{categorization\_strength} \geq 0.35$ and $Score_{dissimilarity} > Score_{similarity}$, then this is an indication that the scores are probably dissimilar. However, this is obviously easy to conclude when one of the scores (e.g. applanation or lateral) is 0. So it must also be demanded in that case a minimum absolute difference of scores (see e.g. Eqn. 31).

$$(Score_{applanation} \neq 0 \text{ and } Score_{lateral} \neq 0); \text{ or} \\ (||Score_{applanation}| - |Score_{lateral}|| > 0.08) \quad \text{(Eqn. 31)}$$

If Eqn. 31 is satisfied, then the likelihood of dissimilarity is more confidently reaffirmed. However, the case where one of the scores (applanation or lateral) is zero has not been ruled out. Since such a condition tends to exaggerate the dissimilarity score, when such a case occurs it is desirable to modulate the dissimilarity score by the magnitude of the non-zero score. See Eqn. 32.

$$Score_{dissimilarity} = Min(1.0, 4 * Max(Score_{applanation}, Score_{lateral})) * Score_{dissimilarity} \quad \text{(Eqn. 32)}$$

If $Score_{dissimilarity} > Score_{similarity}$, then the aspect ratio is calculated in one embodiment using Eqn. 33, otherwise no action is taken.

$$k_{AspectRatio} = k_{AspectRatio} + 0.6 \times (4 \times Score_{Dissimilarity} - k_{AspectRatio}) \quad \text{(Eqn. 33)}$$

At step 526, a temperature tax is adaptively assessed upon the reference mean. First, the latest reference mean is added to an n-point (e.g. 5-point) running average. In one embodiment, the balance of these calculations occurs upon demand at the time that the taxed temperature is required. This is particularly advantageous, as the tax is based upon the current core temperature at the time that it is needed.

Figure 5A:
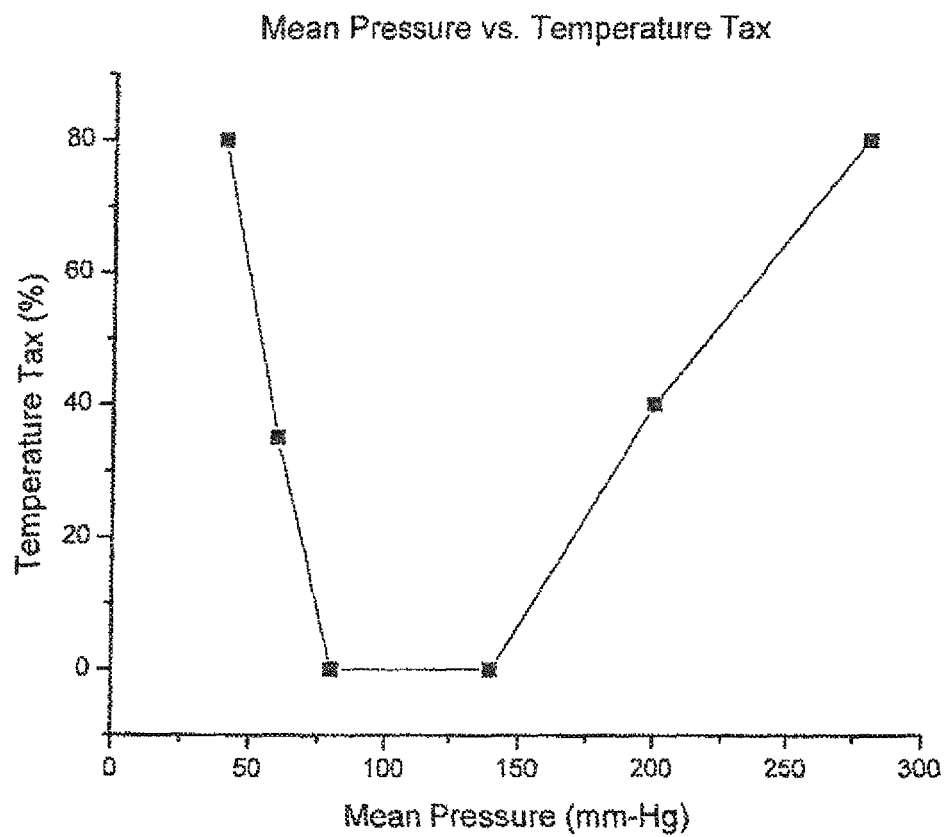
FIG. 5a is a graph illustrating average mean as a function of temperature tax in accordance with one embodiment of the present invention.

Next, a piece-wise linear interpolation is performed on an average mean as a function of temperature tax chart as is shown in FIG. 5a. Upon determining the temperature tax, logic determines if an "alternative minimum tax" (AMT) should be assessed. This AMT is assessed when temperatures go below a certain threshold. This logic asks whether or not the core temperature is below MaxTempForAMT? If so, then use Eqn. 34, otherwise the apparatus uses Eqn. 35.

$$EffectiveTemp = \frac{(CoreTemp + MaxTempForAMT)}{2} \quad \text{(Eqn. 34)}$$

$$EffectiveTemp = CoreTemp \quad \text{(Eqn. 35)}$$

The taxed temperature is then calculated using Eqn. 36.

$$TaxedTemp = EffectiveTemp \times TemperatureTax \quad \text{(Eqn. 36)}$$

System Apparatus for Hemodynamic Assessment

Figure 6:
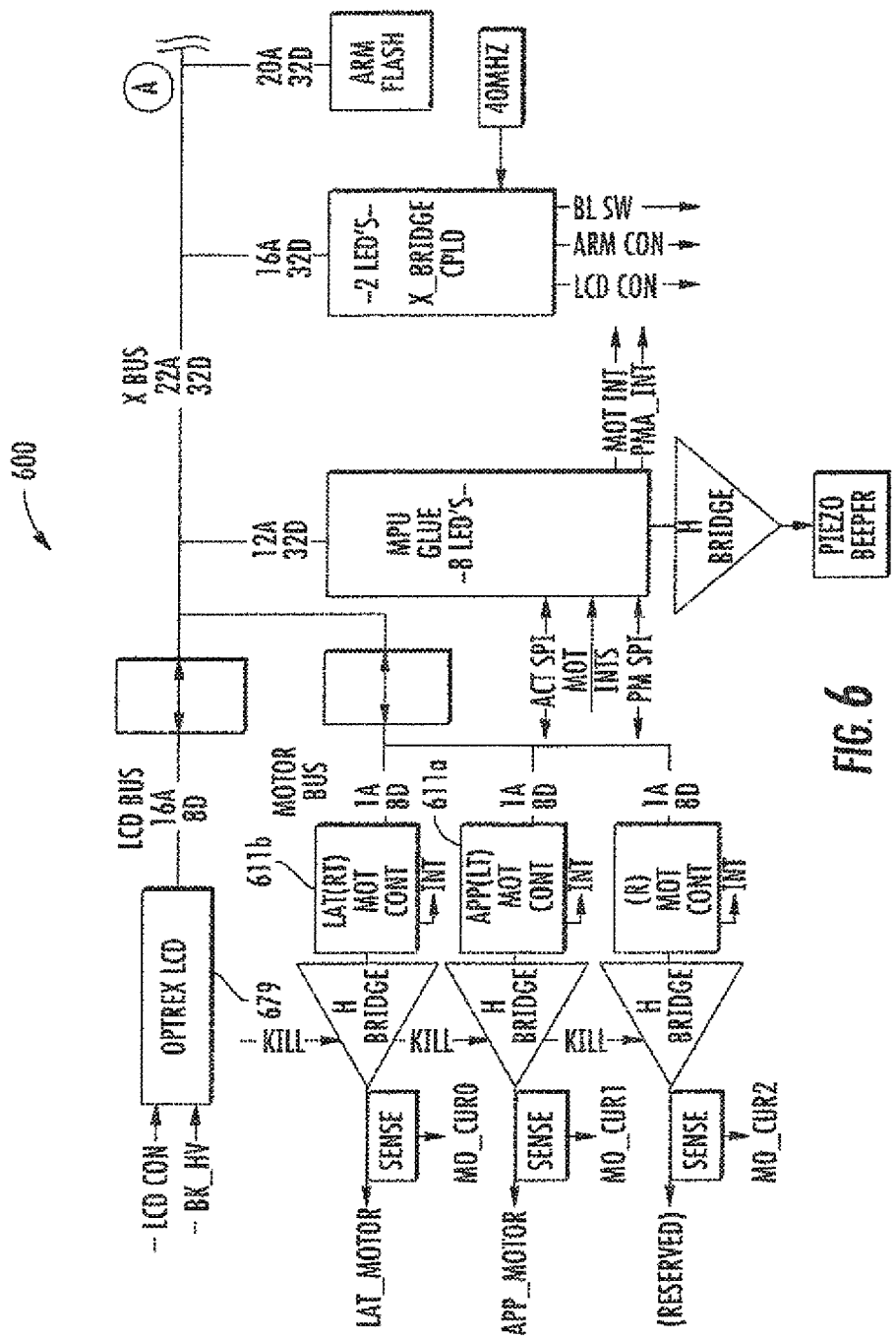
FIG. 6 is a block diagram of one exemplary embodiment of the apparatus for hemodynamic parameter assessment within the blood vessel of a living subject according to the invention.
Figure 6:
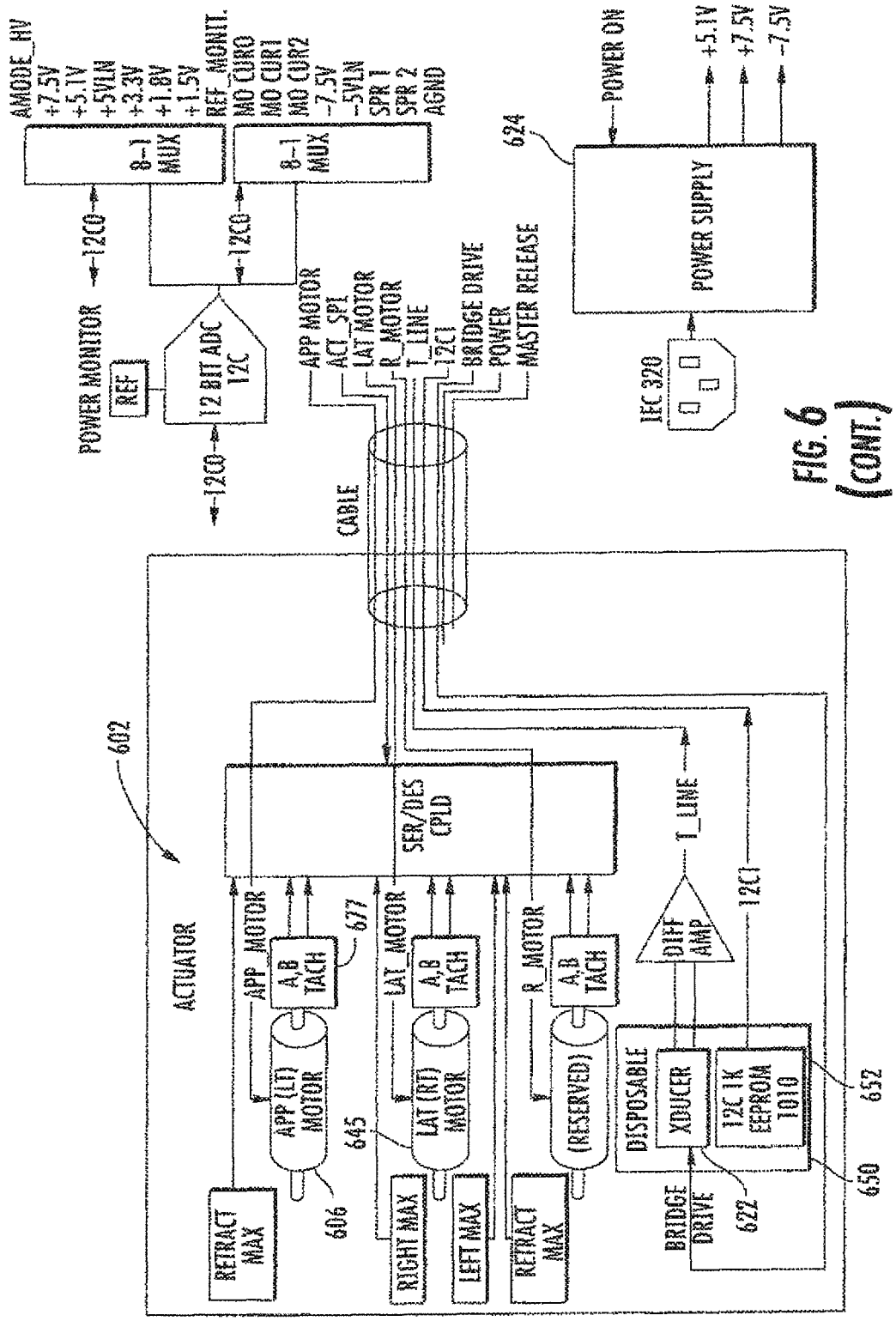
Figure 6:
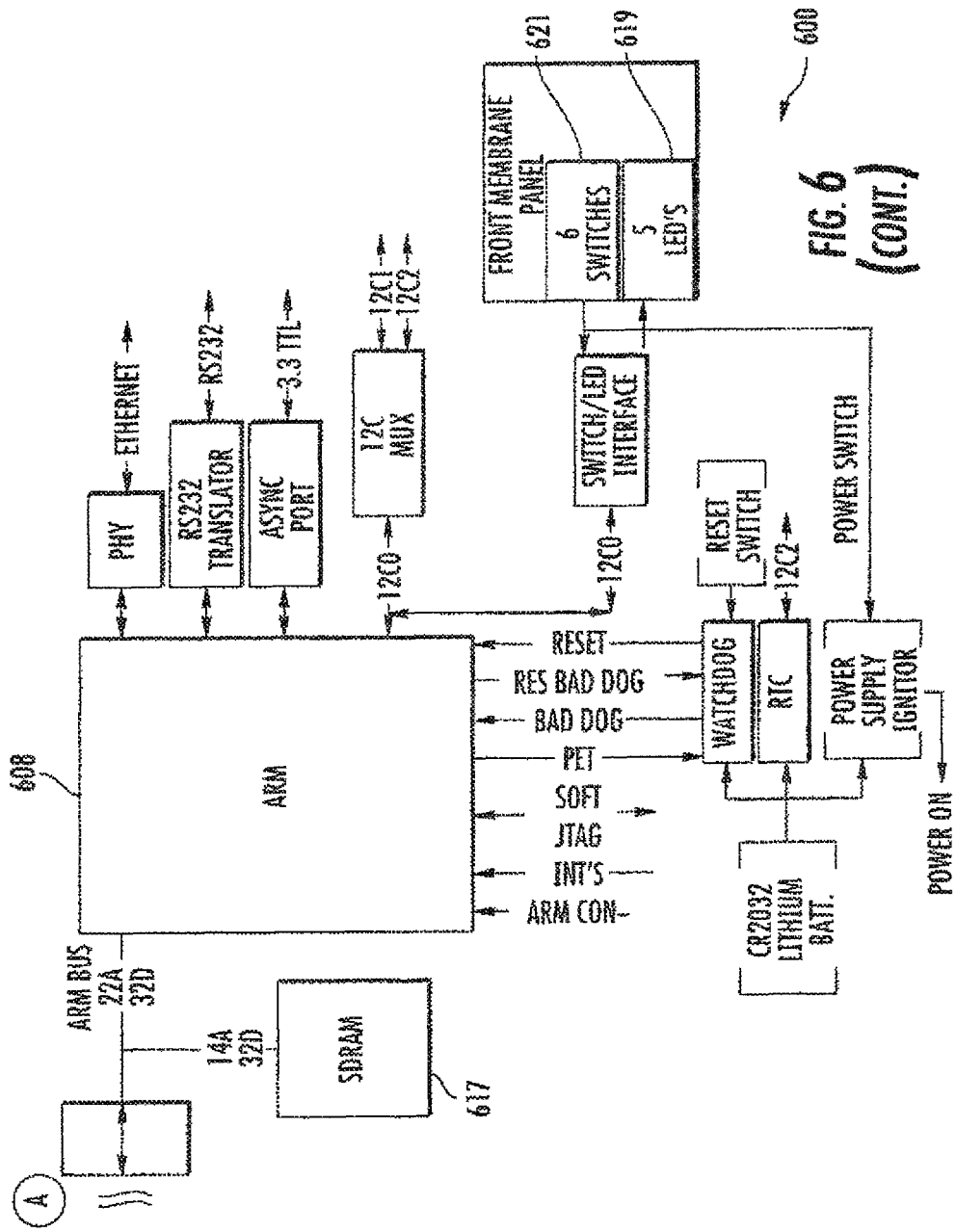
Figure 6:
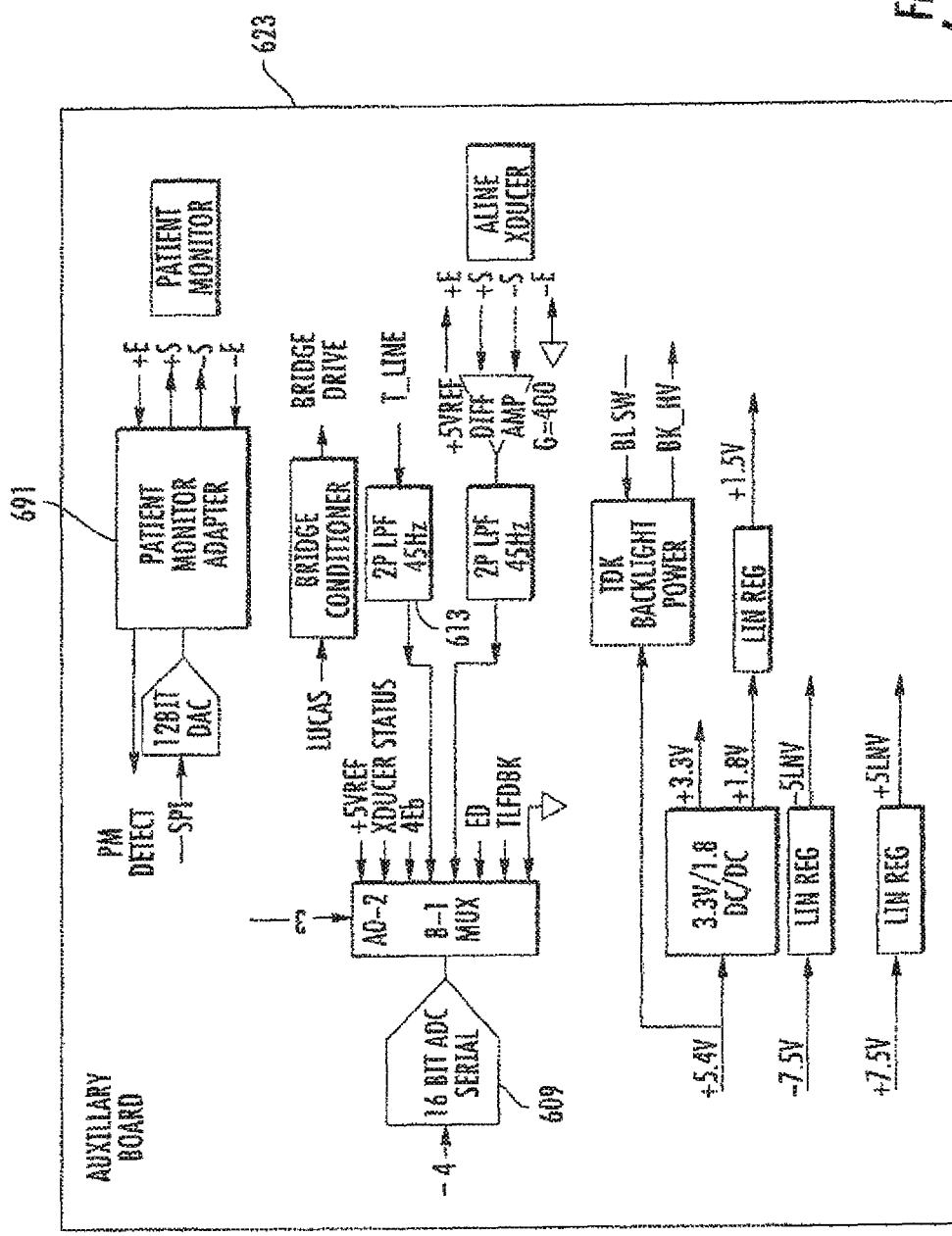

Referring now to FIG. 6, exemplary embodiments of apparatus for measuring hemodynamic properties within the blood vessel of a living subject consistent with the control methodologies of the present invention are now described. In the illustrated embodiment, the apparatus is adapted for the measurement of blood pressure within the radial artery of a human being, although it will be recognized that other hemodynamic parameters, monitoring sites, and even types of living organism may be utilized in conjunction with the invention in its broadest sense.

The exemplary apparatus 600 of FIG. 6 fundamentally comprises an applanation assembly (including one or more pressure transducers 622) for measuring blood pressure from the radial artery tonometrically; a digital processor 608 operatively connected to the pressure transducer(s) 622 (and a number of intermediary components) for (i) analyzing the signals generated by the transducer(s); (ii) generating control signals for the stepper motor 606 (via a microcontroller 611a operatively coupled to the stepper motor control circuits); and (iii) storing measured and analyzed data. The motor controllers 611, processor 608, auxiliary board 623, and other components may be housed either locally to the applanator 602, or alternatively in a separate stand-alone housing configuration if desired. The pressure transducer 622 and its associated storage device 652 are optionally made removable from the applanator 602.

The pressure transducer 622 is, in the present embodiment, a strain beam transducer element which generates an electrical signal in functional relationship (e.g., proportional) to the pressure applied to its sensing surface, although other technologies may be used. The analog pressure signals generated by the pressure transducer 622 are converted into a digital form (using, e.g., an ADC 609) after being optionally low-pass filtered 613 and sent to the signal processor 608 for analysis. Depending on the type of analysis employed, the signal processor 608 utilizes its program either embedded or stored in an external storage device to analyze the pressure signals and other related data (e.g., stepper motor position as determined by the position encoder 677, scaling data contained in the transducer's EEPROM 652 via I2C1 signal).

As shown in FIG. 6, the apparatus 600 is also optionally equipped with a second stepper motor 645 and associated controller 611b, the second motor 645 being adapted to move the applanator assembly 602 laterally across the blood vessel (e.g., radial artery) of the subject as described above. A third stepper motor (not shown) and associated controls may also be implemented if desired to control the proximal positioning of the applanation element 602. Operation of the lateral positioning motor 645 and its controller 611b is substantially analogous to that of the applanation motor 606, consistent with the methodologies previously described herein.

As previously discussed, continuous accurate non-invasive measurements of hemodynamic parameters (e.g., blood pressure) are highly desirable. To this end, the apparatus 600 is designed to (i) identify the proper level of applanation of the subject blood vessel and associated tissue; (ii) continuously "servo" on this condition to maintain the blood vessel/tissue properly biased for the best possible tonometric measurement; optionally; and (iii) scale the tonometric measurement as needed to provide an accurate representation of intravascular pressure to the user/operator.

During the simulated annealing process, the controller 611a controls the applanation motor 606 to applanate the artery (and interposed tissue) according to a predetermined profile. Such control schemes may also be employed with respect to the lateral and proximal motor drive assemblies if desired, or alternatively a more static approach (i.e., position to an optimal initial position, and then reposition only upon the occurrence of an event causing significant misalignment). In this regard, it will be recognized that the control schemes for the applanation motor and the lateral/proximal positioning motor(s) may be coupled to any degree desired consistent with the invention.

The apparatus 600 is also configured to apply the methodologies of the first, second, third and fourth processes 102, 104, 106 and 108 previously discussed with respect to FIGS. 1-5. Details of exemplary implementations of these latter methodologies are described elsewhere herein.

The physical apparatus 600 of FIG. 6 comprises, in the illustrated embodiment, a substantially self-contained unit having, inter glia, a combined pressure transducer 622 and applanation device 600, motor controllers 611, RISC digital processor 608 with associated synchronous DRAM (SDRAM) memory 617 and instruction set (including scaling lookup tables), display LEDs 619, front panel input device 621, and power supply 624. In this embodiment, the controllers 611 are used to control the operation of the combined pressure transducer/applanation device, with the control and scaling algorithms are implemented on a continuing basis, based on initial operator/user inputs.

For example, in one embodiment, the user input interface comprises a plurality (e.g., two) buttons disposed on the face of the apparatus housing (not shown) and coupled to the LCD display 679. The processor programming and LCD driver are configured to display interactive prompts via the display 679 to the user upon depression of each of the two buttons.

Furthermore, a patient monitor (PM) interface circuit 691 shown in FIG. 6 may be used to interface the apparatus 600 to an external or third-party patient monitoring system. Exemplary configurations for such interfaces 691 are described in detail in U.S. patent application Ser. No. 10/060,646 entitled "Apparatus and Method for Interfacing Time-Variant Signals" filed on Jan. 30, 2002 and patented as U.S. Pat. No. 7,317,409 on Jan. 8, 2008, and assigned to the Assignee hereof, which is incorporated by reference herein in its entirety, although other approaches and circuits may be used. The referenced interface circuit has the distinct advantage of automatically interfacing with literally any type of patient monitor system regardless of its configuration. In this fashion, the apparatus 600 of the present invention coupled to the aforementioned interface circuit allows clinicians and other health care professionals to plug the apparatus into in situ monitoring equipment already on hand at their facility, thereby obviating the need (and cost) associated with a dedicated monitoring system just for blood pressure measurement.

Additionally, an EEPROM 652 is physically coupled to the pressure transducer 622 as shown in FIG. 6 so as to form a unitary unit which is removable from the host apparatus 600. The details of the construction and operation of exemplary embodiments of such coupled assemblies are described in detail in co-owned U.S. Pat. No. 6,676,600, entitled "Smart Physiologic Parameter Sensor and Method", issued Jan. 13, 2004, assigned to the Assignee hereof, and incorporated by reference herein in its entirety, although other configurations clearly may be substituted. By using such a coupled and removable arrangement, both the transducer 622 and EEPROM 652 may be readily removed and replaced within the system 600 by the operator.

It is also noted that the apparatus 600 described herein may be constructed in a variety of different configurations, and using a variety of different components other than those specifically described herein. For example, it will be recognized that while many of the foregoing components such as the processor 608, ADC 609, controller 611, and memory are described effectively as discrete integrated circuit components, these components and their functionality may be combined into one or more devices of higher integration level (e.g., so-called "system-on-chip" (SoC) devices). The construction and operation of such different apparatus configurations (given the disclosure provided herein) are readily within the possession of those of ordinary skill in the medical instrumentation and electronics field, and accordingly not described further herein.

The computer program(s) for implementing the aforementioned first, second, third and fourth processes are also included in the apparatus 600. In one exemplary embodiment, the computer program comprises an object ("machine") code representation of a $C^{++}$ source code listing implementing the methodology of FIGS. 1-5, either individually or in combination thereof. While $C^{++}$ language is used for the present embodiment, it will be appreciated that other programming languages may be used, including for example VisualBasic™, FORTRAN, and $C^+$. The object code representation of the source code listing is compiled and may be disposed on a media storage device of the type well known in the computer arts. Such media storage devices can include, without limitation, optical discs, CD ROMs, magnetic floppy disks or "hard" drives, tape drives, or even magnetic bubble memory. These programs may also be embedded within the program memory of an embedded device if desired. The computer program may further comprise a graphical user interface (GUI) of the type well known in the programming arts, which is operatively coupled to the display and input device of the host computer or apparatus on which the program is run.

In terms of general structure, the program is comprised of a series of subroutines or algorithms for implementing the applanation and scaling methodologies described herein based on measured parametric data provided to the host apparatus 600. Specifically, the computer program comprises an assembly language/micro-coded instruction set disposed within the embedded storage device, i.e. program memory, of the digital processor or microprocessor associated with the hemodynamic measurement apparatus 600. This latter embodiment provides the advantage of compactness in that it obviates the need for a stand-alone PC or similar hardware to implement the program's functionality. Such compactness is highly desirable in the clinical and home settings, where space (and ease of operation) are at a premium.

As previously noted, one of the significant advantages of the present invention relates to its flexibility; i.e., that it is essentially agnostic to the hardware/firmware/software on which it is used, and can be readily adapted to various different platforms or systems for measuring hemodynamic or other physiologic parameters. For example, the methods and apparatus of the present invention are substantially compatible with, inter glia, those described in: U.S. patent application Ser. No. 10/393,660 entitled "Method and Apparatus for Control of Non-Invasive Parameter Measurements" filed on Mar. 20, 2003 and patented as U.S. Pat. No. 7,291,112 on Nov. 6, 2007; co-pending U.S. patent application Ser. No. 10/269,801 entitled "Apparatus and Methods for Non-Invasively Measuring Hemodynamic Parameters" filed on Oct. 11, 2002 and published as U.S. Patent Publication No. 2004/0073123 on Apr. 15, 2004; U.S. patent application Ser. No. 10/920,990 entitled "Apparatus and Methods for Non-Invasively Measuring Hemodynamic Parameters" filed on Aug. 18, 2004 and published as U.S. Patent Publication No. 2005/0080345 on Apr. 14, 2005; U.S. patent application Ser. No. 11/336,222 entitled "Apparatus and Methods for Non-Invasively Measuring Hemodynamic Parameters" filed on Jan. 20, 2006 and published as U.S. Patent Publication No. 2006/0184051 on Aug. 17, 2006; U.S. patent application Ser. No. 09/534,900 entitled "Method and Apparatus for Assessing Hemodynamic Parameters within the Circulatory System of a Living Subject" filed on Mar. 23, 2000 and issued as U.S. Pat. No. 6,554,774 on Apr. 29, 2003, each of the foregoing assigned to the Assignee hereof and incorporated by reference herein in its entirety.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. Computer readable apparatus comprising non-transitory media comprising a computer program having a plurality of instructions configured to determine an optimized location for placement of a pressure transducer on a living subject to obtain hemodynamic measurements therefrom, said plurality of instructions configured to, when executed by a processor, cause the processor to:

obtain a first pulse pressure measurement from said pressure transducer at a first location on a skin surface of said living subject;

based at least in part on said pressure measurement, determine a first value indicative of a closeness of said first location to an optimal location;

generate a trial sequence;

direct said pressure transducer to relocate to at least one second location in accordance with said trial sequence;

obtain pressure measurements from said pressure transducer at said at least one second location; and based at least in part on said pressure measurements obtained, determine a second value, said second value being indicative of a closeness of said at least one second location to said optimal location.

2. The apparatus of claim 1, wherein said trial sequence comprises a substantially random trial sequence having at least one reference point and at least one dither, a size of said dither configured to vary as a function of said second value.

3. The apparatus of claim 1, wherein when said second value indicates at least a predetermined level of closeness of said at least one second location to said optimal location, said plurality of instructions are further configured to monitor at least one hemodynamic parameter at said second location.

4. The apparatus of claim 1, wherein when said second value does not indicate at least a predetermined level of closeness to said optimal location, said plurality of instructions are further configured to:

generate a second trial sequence based at least in part on said first dither sequence;

direct said pressure transducer to relocate to at least one third location;
obtain pressure measurements at said at least one third location; and
determine a third value, said third value being indicative of a closeness of said at least one third location to said optimal location.

5. The apparatus of claim 1, wherein when said pressure measurements obtained at said first or said at least one second location are outside of a predetermined pressure range, said plurality of instructions are further configured to apply a quantity to said value associated therewith.

6. Transient-resistant apparatus configured to determine a blood pressure of a living subject, said apparatus comprising:
a pressure transducer configured to be disposed proximate a blood vessel of said living subject and obtain pressure signals therefrom; and
a processor configured to run a computer program thereon, said computer program comprising a plurality of instructions which are configured to, when executed:
perform at least one simulated annealing related algorithm to control a placement of said pressure transducer, and to maintain said pressure transducer in an optimized operational state;
obtain first data regarding hemodynamic parameters measured by said pressure transducer at a first location on said subject;
obtain second data regarding hemodynamic parameters measured by said pressure transducer at one or more different locations on said subject; and
determine an optimized location by:
apply a correction factor to said obtained first and second data;
calculate a difference between a closeness of said one or more different locations to an optimized location and a value assigned to a closeness of said first location to said optimized location; and
based at least in part on said difference, determination of a size of a dither value.

7. The apparatus of claim 6, wherein said pressure transducer comprises a component of an applanation assembly, said assembly in communication with said processor and configured to cause a removable applanator to applanate said blood vessel.

8. The apparatus of claim 7, wherein said removable applanator is configured to vary a level of applanation of said blood vessel in order to maintain said blood vessel in a substantially optimal state of compression to obtain said signals.

9. The apparatus of claim 6, wherein said plurality of instructions are further configured to, when executed:
analyze signals produced by said pressure transducer;
generate control signals for a motor configured to adjust a position of said pressure transducer; and
store data regarding said analyzed signals.

10. The apparatus of claim 6, wherein said plurality of instructions are further configured to obtain said second data regarding hemodynamic parameters measured by said pressure transducer at said one or more different locations on said living subject via:
placement of said pressure transducer at a first one of said different locations;
applanation of a blood vessel located proximate thereto;
measurement of pulse beats; and
determination of whether to re-locate said pressure transducer to another one of said different locations based, at least in part, on said measured pulse beats.

11. A method of determining hemodynamic parameters of a living subject via a pressure transducer disposed on said subject, said pressure transducer configured to applanate said subject's tissue and detect pulse beats, said method comprising:
executing a randomly determined trial sequence;
calculating an average pulse pressure over a predetermined number of beats;
processing a plurality of data;
adjusting one or more parameters based at least in part on results obtained from said act of processing; and
when no beats are detected:
moving said pressure transducer a predetermined distance while simultaneously continuously varying applanation pressure until said predetermined number of beats are detected; and
repositioning said pressure transducer over a position of said living subject's tissue at a position where said predetermined number of beats are detected.

12. The method of claim 11, wherein said act of execution said trial sequence comprises setting a target position and moving said pressure transducer to said target position; and
wherein a distance between said target position and an original position of said pressure transducer is configured to vary as a function of a value associated with a closeness of said original position to an optimal position.

13. The method of claim 12, wherein said act of processing said plurality of data comprises:
utilizing a correction factor to adjust pulse pressure measurements in said plurality of data to more closely approximate mean pressure measurements; and
assigning a value to a closeness of said target position to said optimal position based at least in part on said adjusted pulse pressure measurements.

14. The method of claim 13, wherein said act of adjusting one or more parameters comprises adjusting a size of a dither, said size of said dither being determined based at least in part on a comparison of said value assigned to said closeness of said target position to said optimal position, and a value assigned to an initial plurality of data; and
wherein said method further comprises executing said dither.

15. A method of determining hemodynamic parameters of a living subject via a pressure transducer disposed on said living subject, said pressure transducer configured to applanate said living subject's tissue and obtain an initial plurality of data of measured pulse pressure; said method comprising:
executing a randomly determined trial sequence by setting a target position and moving said pressure transducer to said target position;
obtaining a second plurality of data regarding measured pulse pressure at least during said act of executing;
processing said second plurality of data; and
adjusting one or more parameters based at least in part on results obtained from said act of processing;
wherein a distance between said target position and an original position of said pressure transducer is configured to vary as a function of a value associated with a closeness of said original position to an optimal position.

16. The method of claim 15, wherein at least one of said act of obtaining an initial plurality of data and said act of obtaining said second plurality of data comprises:
detecting pulse beats; and
calculating an average pulse pressure over a predetermined number of beats.

17. The method of claim 16, wherein said method further comprises, when no beats are detected:
- moving said pressure transducer a predetermined distance while simultaneously continuously varying applanation pressure until said predetermined number of beats are detected; and
- repositioning said pressure transducer over a position of said living subject's tissue at a position where said predetermined number of beats are detected.

18. The method of claim 15, wherein said act of processing said second plurality of data comprises:
- utilizing a correction factor to adjust pulse pressure measurements in said second plurality of data to more closely approximate mean pressure measurements; and
- assigning a value to a closeness of said target position to said optimal position based at least in part on said adjusted pulse pressure measurements.

19. The method of claim 18, wherein said act of adjusting one or more parameters comprises adjusting a size of a dither, said size of said dither being determined based at least in part on a comparison of said value assigned to said closeness of said target position to said optimal position, and a value assigned to said initial plurality of data; and
- wherein said method further comprises executing said dither.

* * * * *